US011365404B2

(12) United States Patent
Kubo et al.

(10) Patent No.: US 11,365,404 B2
(45) Date of Patent: Jun. 21, 2022

(54) METHOD FOR OBTAINING NUCLEIC ACID DERIVED FROM FETAL CELL

(71) Applicant: TL Genomics Inc., Tokyo (JP)

(72) Inventors: Tomohiro Kubo, Tokyo (JP); Madoka Ayano, Tokyo (JP); Tomomi Ando, Tokyo (JP)

(73) Assignee: TL Genomics Inc., Tokyo (JP)

( * ) Notice: Subject to any disclaimer, the term of this patent is extended or adjusted under 35 U.S.C. 154(b) by 438 days.

(21) Appl. No.: 16/473,046

(22) PCT Filed: Oct. 18, 2017

(86) PCT No.: PCT/JP2017/037706
§ 371 (c)(1),
(2) Date: Jun. 24, 2019

(87) PCT Pub. No.: WO2018/123220
PCT Pub. Date: Jul. 5, 2018

(65) Prior Publication Data
US 2020/0087654 A1 Mar. 19, 2020

(30) Foreign Application Priority Data
Dec. 27, 2016 (JP) .............................. JP2016-253589

(51) Int. Cl.
*C12N 15/10* (2006.01)
*B01L 3/00* (2006.01)
*C12Q 1/6869* (2018.01)
*G01N 1/28* (2006.01)

(52) U.S. Cl.
CPC .... *C12N 15/1003* (2013.01); *B01L 3/502761* (2013.01); *C12Q 1/6869* (2013.01); *G01N 1/28* (2013.01); *B01L 2200/0647* (2013.01)

(58) Field of Classification Search
CPC ................ C12N 15/1003; C12N 15/09; C12N 15/1013; C12N 5/02; B01L 3/502761; C12Q 1/6869; C12Q 1/06; C12Q 1/24; C12Q 1/68; C12Q 1/6806; G01N 1/28; G01N 33/53; G01N 37/00; G01N 33/56966; G01N 33/56972; C12M 3/04
See application file for complete search history.

(56) References Cited

U.S. PATENT DOCUMENTS

| 5,731,156 | A | 3/1998 | Golbus |
| 5,962,234 | A | 10/1999 | Golbus |
| 6,949,355 | B2* | 9/2005 | Yamanishi .......... A61M 1/3616 435/34 |
| 7,785,898 | B2 | 8/2010 | Bohmer |
| 2010/0196897 | A1 | 8/2010 | Manaresi et al. |
| 2012/0301867 | A1 | 11/2012 | Kumo et al. |
| 2013/0037623 | A1 | 2/2013 | Yamaguchi |
| 2013/0072402 | A1* | 3/2013 | Takamura ............ C12N 5/0087 506/9 |
| 2014/0057799 | A1 | 2/2014 | Johnson et al. |
| 2014/0141997 | A1* | 5/2014 | Mahyuddin ............ G01N 33/80 506/9 |
| 2015/0330979 | A1* | 11/2015 | Bennani ............... C12Q 1/6806 506/9 |

FOREIGN PATENT DOCUMENTS

| AU | 667723 B2 | 12/1993 |
| JP | H06-509178 A | 10/1994 |
| JP | 2007-175684 A | 7/2007 |
| JP | 2007-530629 A | 11/2007 |
| JP | 4091123 B2 | 5/2008 |
| JP | 2009-511001 A | 3/2009 |
| JP | 5265815 B2 | 8/2013 |
| JP | 5308834 B2 | 10/2013 |
| JP | 5311356 B2 | 10/2013 |
| JP | 2014-223082 A | 12/2014 |
| JP | 5642537 B2 | 12/2014 |
| JP | 2015-515263 A | 5/2015 |
| JP | 2015-158489 A | 9/2015 |
| JP | 5857537 B2 | 2/2016 |
| JP | 2016-067268 A | 5/2016 |
| WO | 9503431 A1 | 2/1995 |

(Continued)

OTHER PUBLICATIONS

Byeon et al, Isolation of nucleated red blood cells in maternal blood for Non-invasive prenatal diagnosis, 2015, Biomed Microdevices, 17, 18, pp. 1-7 (Year: 2015).*
Korean Office Action dated Jul. 28, 2020, in connection with corresponding KR Application No. 10-2019-7022034 (11 pp., including machine-generated English translation).
International Search Report dated Feb. 13, 2018 in corresponding International Application No. PCT/JP2017/037706; 3 pages.
Taizan Kamide et al., "New Trials for Efficient Erythroblast Isolation From Maternal Blood", Sei-i-Kai, Tokyo Jikeikai Medical Journal, 2015, 130: 11-7; Partial English translation included.
Vijay G. Sankaran et al., "The Switch from Fetal to Adult Hemoglobin", Cold Spring Harbor Perspectives in Medicine 2013; 3: a011643; pp. 1-14.
Iain C Macaulay et al., "G&T-seq: parallel sequencing of single-cell genomes and transcriptomes", Nature Methods, vol. 12 No 6, Jun. 2015; 7 pages.

(Continued)

*Primary Examiner* — Narayan K Bhat
(74) *Attorney, Agent, or Firm* — Maier & Maier, PLLC

(57) ABSTRACT

In the present invention, a fraction (A) is labeled, the fraction (A) being a fraction obtained from a maternal blood sample and in which nucleated red blood cells (NRBCs) are concentrated in a population of whole blood cells. Then, a fraction (B) having increase purity of NRBCs is obtained by sorting out blood cells in the labeled fraction A by at least cell sorting. Next, fractions (C) are obtained by separating each blood cell in the fraction (B) at a single-cell level and independently performing a process for extracting a nucleic acid for each separated blood cell, each of the fractions (C) containing a nucleic acid distinguishable at a single-cell level. Then, a fraction (D) containing a nucleic acid derived from a fetus is sorted out from a group of fractions (C) by performing a molecular biological analysis for each of the fractions (C).

19 Claims, 21 Drawing Sheets

(56) References Cited

FOREIGN PATENT DOCUMENTS

| WO | 2005/100401 A2 | 10/2005 |
|---|---|---|
| WO | 2007/035498 A2 | 3/2007 |
| WO | 2008/135837 A2 | 11/2008 |
| WO | 2012/162267 A2 | 11/2012 |
| WO | 2013/130714 A1 | 9/2013 |

OTHER PUBLICATIONS

Canadian Office Action dated Jun. 25, 2020, in connection with corresponding CA Application No. 3,047,709 (6 pp.).
Wapner, Ronald J. et al. "Chromosomal Microarray versus Karyotyping for Prenatal Diagnosis." The New England Journal of Medicine. Dec. 6, 2012. pp. 2175-2184. vol. 367, No. 23.
Canadian Office Action dated May 26, 2021, in connection with CA Application No. 3,047,709; 6 pages.
European Extended Search Report dated Oct. 26, 2020, in connection with corresponding EP Application No. 17887449.1; 20 pages.
Gross, A., et al. "Technologies for Single-Cell Isolation," International Journal of Molecular Sciences, Jul. 24, 2015, pp. 16897-16919, vol. 16, No. 8.
Singaporean Office Action dated Oct. 5, 2020, in connection with corresponding SG Application No. 11201905613X; 9 pages.
European Search Report dated Jul. 14, 2020, in corresponding European patent application No. 17887449.1, 8 pages.
Cha et al., "A simple and sensitive erythroblast scoring system to identify fetal cells in maternal blood", Prenatal Diagnosis, Prenat Diagn 2003, vol. 23, Jan. 1, 2003, pp. 68-73.
Office Action dated Dec. 20, 2021, in connection with corresponding Indian Application No. 201917026451; 7 pages with English Translation.

* cited by examiner

METHOD FOR OBTAINING NUCLEIC ACID DERIVED FROM FETAL CELL

FIELD

The present invention relates to a method for obtaining chromosomal DNA of fetal cell origin in maternal blood sample.

BACKGROUND

Attempts to develop a method for collecting chromosomal DNA of fetal cell origin with high purity have been continued in order to perform noninvasive prenatal genetic testing (NIPT). Attempts have been made to concentrate nucleated red blood cells (NRBCs) derived from a fetus in maternal blood for the purpose of collecting chromosomal DNA of fetal cell origin.

Each of Japanese Patent No. 5265815, Japanese Patent No. 5311356, Japanese Unexamined Patent Application Publication No. 2009-511001, and Published Japanese Translation of PCT International Publication for Patent Application, No. H06-509178 discloses a method for concentrating NRBCs in a maternal blood sample. In these patent literatures, a density gradient centrifugation method is used. Japanese Patent No. 5311356 further uses a microchannel chip. Japanese Unexamined Patent Application Publication No. 2009-511001 uses a magnetic field.

SUMMARY

As shown in paragraph 0164 of Japanese Unexamined Patent Application Publication No. 2009-511001, when a maternal blood sample is analyzed by FACS, nucleated cells in which the expression of CD71 (TFRC, Transferrin receptor protein 1) and CD235a (GPA, Glycophorin A) is detected, i.e. NRBCs account for no more than 0.15% of mono-nuclear cells in maternal blood. Nucleated cells in maternal blood are mainly occupied by white blood cells (WBCs) of maternal origin.

Even in fractions of NRBCs obtained by one of the above-mentioned concentration methods, WBCs of maternal origin are still major blood cells in some cases. Therefore, there is a possibility that DNA of WBCs of maternal origin could be mixed in chromosomal DNA of fetal cell origin obtained from such fractions. Further, NRBCs of maternal origin are also contained in maternal blood. Therefore, it is all the more difficult to obtain chromosomal DNA of fetal cell origin with high purity.

Japanese Unexamined Patent Application Publication No. 2016-067268 discloses a method in which candidate cells for NRBCs are isolated by morphologically observing blood cells on a slide glass (paragraphs 0069 and 0070). In this method, a coating of NRBCs concentrated by a density gradient centrifugation method is applied to a slide glass and then the blood cells are stained by May-Giemsa stain (paragraphs 0066 to 0068). Further, it is checked whether or not the isolated candidate cells for NRBCs are cells derived from a fetus by a molecular biological analysis (paragraph 0079).

The present invention provides a method for obtaining chromosomal DNA of fetal cell origin from a maternal blood sample. An object of the present invention is to provide a method capable of obtaining chromosomal DNA derived from a nucleated red blood cell (NRBC) derived from a fetus isolated at a single-cell level.

[P1] A method for obtaining chromosomal DNA of fetal cell origin, including:
  a. specifically labeling red blood cells (RBCs) and nucleic acids in a fraction A, the fraction A being a fraction which is obtained from a maternal blood sample and in which NRBCs are concentrated in a population of whole blood cells;
  b. obtaining a fraction B having increased purity of NRBCs by sorting out the labeled blood cells in the fraction A by at least cell sorting;
  c. obtaining fractions C by separating each blood cell in the fraction B at a single-cell level and independently performing a process for extracting chromosomal DNA for each of the separated blood cells, each of the fractions C containing chromosomal DNA distinguishable at a single-cell level; and
  d. selecting a fraction D containing chromosomal DNA derived from a fetus from a group of the fractions C by performing a molecular biological analysis for each of the fractions C.

[P2] The method described in [P1], in which the fraction A is a fraction obtained by removing at least some of non-nucleated RBCs from blood cells in the maternal blood sample.

[P3] The method described in [P2], in which the fraction A is a fraction obtained by fractionating the blood cells in the maternal blood sample based on at least one property of their volumetric mass densities and their sizes.

[P4] The method described in [P3], in which,
  in the step c, the fraction C is obtained by indiscriminately performing the separation of blood cells in the faction B at the single-cell level irrespective of whether or not each of the blood cells in the fraction B has a characteristic of an NRBC, and indiscriminately performing the process for extracting chromosomal DNA, and
  since the fraction C is indiscriminately obtained, it is presumed that the chromosomal DNA contained in the fraction D was originated from an NRBC in an after-the-fact manner based on a determination that the chromosomal DNA is derived from a fetus made in the step d.

[P5] The method described in [P4], in which,
  in the step c, fractions E are obtained by fractionizing the fraction B by a limited dilution method, each of the fractions E containing a blood cell separate at a single-cell level, and
  the fraction C is obtained by performing the process for extracting chromosomal DNA for each of the fractions E.

[P6] The method described in [P5], further including:
  indiscriminately sorting a fraction F from the fraction B;
  photographing the fraction F; and
  determining whether or not the fraction F is obtained as the fraction E by checking that a blood cell separated at a single-cell level is contained in the fraction F by using an image of the fraction F.

[P7] The method described in any one of [P3] to [P6], in which the labeling and the cell sorting are performed without performing histological crosslinking/fixing for blood cells in the fractions A.

[P8] The method described in any one of [P3] to [P7], in which
  in the step a, the labeling is performed by using fluorescent labeling,
  in the step b, a liquid flow containing the fraction A is formed in a cell sorter,
  the labeled blood cells are separated from the liquid flow by generating pulsed flows in a direction intersecting the liquid flow while using the labeled blood cells in the liquid flow as targets, and making the labeled blood cells carried by the pulsed flows, and the fraction B is generated by successively collecting the separated blood cells.

[P9] The method described in any one of [P3] to [P8], in which in the step a, the fraction A is a fraction obtained by further removing, by an immunological removal method, WBCs from the fraction obtained by fractionating blood cells in the maternal blood sample based on at least their volumetric mass densities or their sizes.

[P10] The method described in [P3], in which in the step a, the labeling is performed by using fluorescent labeling, in the step b, a fraction G having increased purity of NRBCs is obtained by sorting out the fluorescent-labeled blood cells in the fraction A by cell sorting;

the fraction B having further-increased purity of NRBCs is obtained by spreading blood cells contained in the fraction G on a planar chip and sorting them from the planar chip;

in the step c, the fraction C is obtained by indiscriminately performing the separation of blood cells in the faction B at the single-cell level and indiscriminately performing the process for extracting chromosomal DNA, and since the fraction C is indiscriminately obtained, it is presumed that the chromosomal DNA contained in the fraction D was originated from an NRBC in an after-the-fact manner based on a determination that the chromosomal DNA is derived from a fetus made in the step d.

[P11] The method described in any one of [P3] to [P10], further including obtaining the fraction A by fractionating the maternal blood sample based on the volumetric mass density or the size of blood cells.

[P12] The method described in [P11], in which the maternal blood sample is fractionated based on the size of blood cells by processing the maternal blood sample by using a blood-cell separation chip.

[P13] The method described in [P12], in which the blood-cell separation chip includes a main channel, a removal channel connected to the main channel, and a recovery channel connected to the main channel downstream from the removal channel, the maternal blood sample flows through the main channel, non-nucleated RBCs are removed from the maternal blood sample at the removal channel and NRBCs are collected from the maternal blood sample at the recovery channel, so that the fraction A is obtained from the recovery channel, an inscribed diameter of the removal channel is 12 to 19 µm, and an inscribed diameter of the recovery channel is 20 to 30 µm.

[P14] A method including:

analyzing chromosomal DNA in the fraction D obtained by a method described in any one of [P1] to [P13] by a micro-array or a sequencing method; and obtaining data used for a diagnosis in noninvasive prenatal genetic testing from a result of the analysis.

[R1] A method for obtaining a nucleic acid derived from a fetus, including:

a. specifically labeling WBCs and cell nuclei in a fraction A, the fraction A being a fraction which is obtained from a maternal blood sample by fractionizing blood cells in the maternal blood sample based on either or both of their volumetric mass densities and their sizes, and in which NRBCs are concentrated in a population of whole blood cells;

b. obtaining a fraction B containing NRBCs of maternal origin and NRBCs derived from a fetus by sorting out the labeled blood cells in the fraction A by at least cell sorting, in which the sorting-out is performed so that blood cells labeled by a WBCs specific label are removed and blood cells labeled by a label specific to the cell nuclei are collected;

c. obtaining fractions C by separating each of blood cells in the fraction B at a single-cell level irrespective of whether or not the blood cell is an NRBC, and performing a process for extracting a nucleic acid for each of the blood cells separated at the single-cell level irrespective of whether or not the blood cell is an NRBC, each of the fractions C containing a nucleic acid distinguishable at the single-cell level; and d. selecting a fraction D containing a nucleic acid derived from a fetus distinguishable at a single-cell level from a group of the fractions C by performing a molecular biological analysis for each of the fractions C.

[R2] The method described in [R1], in which in the step c, since the fraction C is obtained by a method in which it is not determined whether or not a blood cell was derived from an NRBC, it is presumed that a nucleic acid contained in the fraction D was originated from an NRBC separated at a single-cell level in an after-the-fact manner based on a determination that the nucleic acid is derived from a fetus made in the step d.

[R3] The method described in [R1] or [R2], in which the maternal blood sample is maternal blood itself or a non-concentrated sample in which NRBCs are not concentrated in a population of whole blood cells as compared to the maternal blood, and the fraction A is a fraction obtained from the maternal blood sample by fractionating blood cells in the maternal blood sample based on their sizes and removing at least some of non-nucleated RBCs from the blood cells in the maternal blood sample.

[R4] The method described in [R3], in which blood cells of the maternal blood sample are fractionated based on their sizes by processing the maternal blood sample by using a blood-cell separation chip, the blood-cell separation chip includes a main channel, a sub channel connected to a side of the main channel, and a removal channel connected to a side of the main channel downstream from the sub channel, the side of the main channel on which the removal channel is connected being opposite to the side thereof on which the sub channel is connected, the maternal blood sample flows through the main channel, a liquid flowing out from the sub channel pushes blood cells flowing through the main channel from the side of the main channel toward the removal channel, non-nucleated RBCs are removed from the maternal blood sample at the removal channel and NRBCs are collected from the maternal blood sample in a place in the main channel downstream from a connection point of the removal channel, so that the fraction A is obtained, and an inscribed diameter of the removal channel is 12 to 19 µm

[R5] The method described in [R4], in which the blood-cell separation chip further includes a recovery channel connected to a side of the main channel downstream from the removal channel, the side of the main channel on which the recovery channel is connected being opposite to the side thereof on which the sub channel is connected, a liquid flowing out from the sub channel further pushes blood cells flowing through the main channel from the side of the main channel toward the recovery channel, NRBCs are collected from the maternal blood sample at the recovery channel, so that the fraction A is obtained from the recovery channel, and an inscribed diameter of the recovery channel is 20 to 30 μm.

[R6] The method described in any one of [R1] to [R5], in which in the step c, fractions E are obtained by fractionizing the fraction B by a limited dilution method and the fraction C is obtained by performing the process for extracting the nucleic acid for each of the fractions E, each of the fractions E containing a blood cell separated at a single-cell level.

[R7] The method described in [R6], further including:

obtaining a fraction F by sorting blood cells from the fraction B irrespective of whether or not the blood cells are NRBCs, photographing the fraction F; and determining whether or not the fraction F is obtained as the fraction E by checking that a blood cell separated at a single-cell level is contained in the fraction F by using an image of the fraction F, while it is not determining whether or not the blood cell separated at the single-cell level is an NRBC from the image of the fraction F.

[R8] The method described in any one of [R1] to [R5], in which in the step c, the fraction C is obtained by using a fluid device including a channel, a plurality of trapping structures successively arranged along the channel and connected to the channel, and reaction structures provided for respective trapping structures, and separating blood cells contained in the fraction B from each other at a single-cell level by distributing the blood cells to respective trapping structures through the channel, and after trapping the blood cells in the respective trapping structures, obtaining the fraction C in the reaction structures by dissolving the trapped cells and washing out the dissolved substance from the trapping structures toward the reaction structures.

[R9] The method described in any one of [R1] to [R8], in which in the step a, the labeling for at least the nucleic acid is performed by using fluorescent labeling, and in the step b, blood cells that have been specifically fluorescent-labeled for at least the nucleic acid in the fraction A are sorted out by cell sorting based on a fluorescence activated cell sorting method.

[R10] The method described in any one of [R1] to [R9], in which

In the step c, the nucleic acid contained in the fraction C is chromosomal DNA, in the step d, the whole genome of the chromosomal DNA or a partial area in the genome is amplified in order to perform a molecular biological analysis, and the fraction D containing DNA is sorted out as the nucleic acid derived from a fetus, the DNA being an amplification product.

[R11] The method described in any one of [R1] to [R9], in which in the step c, the nucleic acid contained in the fraction C is RNA, the RNA is either or both of an mRNA and a non-coding RNA, in the step d, reverse transcription of the RNA is performed in order to perform a molecular biological analysis, and the fraction D containing a cDNA is sorted out as the nucleic acid derived from a fetus, the cDNA being a reverse-transcription product.

[R12] The method described in [R11], in which in the step c, fractions W associated with respective fractions C are further obtained by extracting chromosomal DNA from each blood cell at the same time when the RNA is extracted, and obtaining a fraction Z associated with the fraction D from a group of the fractions W as a fraction containing chromosomal DNA derived from a fetus distinguishable at a single-cell level.

[R13] A method including:

analyzing a sequence of the nucleic acid in the fraction D obtained by a method according to any one of [R1] to [R12] by a micro-array or a sequencing method; and obtaining data used for a diagnosis in noninvasive prenatal genetic testing from a result of the analysis.

[R14] A method for obtaining chromosomal DNA of fetal cell origin, including:

a. specifically labeling RBCs and nucleic acids in a fraction A, the fraction A being a fraction which is obtained from a maternal blood sample and in which NRBCs are concentrated in a population of whole blood cells, wherein nucleic acids are labeled at least by using fluorescent labeling;

b. obtaining a fraction B having an increased purity of NRBCs by sorting out at least the labeled blood cells in the fraction A by cell sorting, in which blood cells in the fraction A which have been specifically fluorescent-labeled for at least nucleic acids are sorted out by cell sorting based on a fluorescence activated cell sorting method;

c. obtaining fractions C by indiscriminately separating each of blood cells in the fraction B at a single-cell level and indiscriminately and independently performing a process for extracting chromosomal DNA for each of the separated blood cells, each of the fractions C containing chromosomal DNA distinguishable at a single-cell level; and d. selecting a fraction D containing chromosomal DNA derived from a fetus distinguishable at a single-cell level from a group of the fractions C by performing a molecular biological analysis for each of the fractions C, in which since the fraction C is indiscriminately obtained, it is presumed that the chromosomal DNA contained in the fraction D was originated from an NRBC separated at the single-cell level in an after-the-fact manner based on a determination that the chromosomal DNA is derived from a fetus made in the step d, the fraction A is obtained by fractionizing blood cells in a maternal blood sample based on either their volumetric mass densities or their sizes, in the step c, fractions E are obtained by fractionizing the fraction B by a limited dilution method, each of the fractions E containing a blood cell separated at a single-cell level, and the fraction C is obtained by performing the process for extracting the chromosomal DNA for each of the fractions E, and NRBCs of maternal origin and NRBCs derived from a fetus are contained in the fraction B.

[R15] The method described in [R14], in which in the step a, WBCs are labeled specifically in the fraction A in an additional manner, and in the step b, the fraction B is obtained by sorting out blood cells in the labeled blood cells in the fraction A by cell sorting, the fraction B being a fraction in which blood cells labeled by a WBCs specific label are removed.

[R16] The method described in [R14] or [R15], in which
in the step a, the labeling for RBCs is performed by magnetic labeling,
in the step b, blood cells in the fraction A which have been specifically magnetic-labeled for RBCs are sorted out by cell sorting based on a cell sorting method using magnetic labeling before or after the cell sorting based on the fluorescence activated cell sorting method, or
in the step a, the labeling for RBCs is performed by using fluorescent labeling, and
in the step b, blood cells in the fraction A which have been specifically fluorescent-labeled for nucleic acids and RBCs are sorted out by cell sorting based on the fluorescence activated cell sorting method.

The method according to the present invention is characterized in that the fact that a collected chromosomal DNA is derived from an NRBC originated from a fetus isolated at a single-cell level is found out after the process for extraction the chromosomal DNA. As a result, in the present invention, it is possible to obtain chromosomal DNA derived from an NRBC originated from a fetus isolated at a single-cell level.

DRAWINGS BRIEF DESCRIPTION OF THE DRAWINGS

DETAILED DESCRIPTION

First Embodiment

Figure 1:
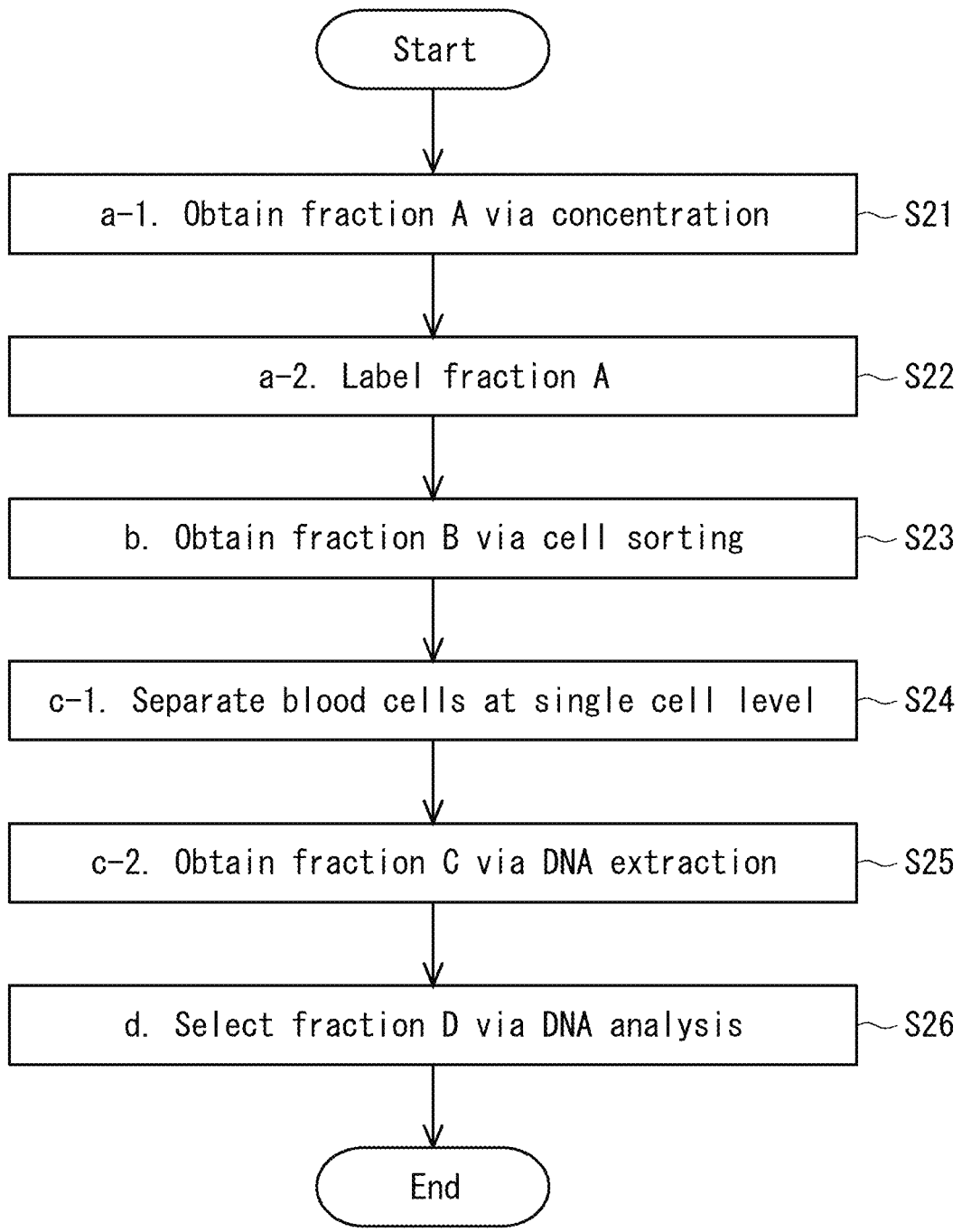
FIG. 1 is a flow chart for an acquisition of chromosomal DNA.

In the below-shown <<First Embodiment>> and its Examples 1 and 2, chromosomal DNA derived from an NRBC originated from a fetus is obtained through processes shown in FIG. 1. Firstly, a maternal blood sample, which is a starting material, is described.

[Collecting Blood]

In this embodiment, the starting material is a maternal blood sample of a human pregnant woman. For pregnant women, the fetal age after menstruation is preferably from 10 weeks to 33 weeks. The fetal age after menstruation is expressed by the number of completed days or completed weeks while defining the first day of the last menstrual period as the first day. The fetal age after menstruation may be calculated by adding two weeks to the fetal age after fertilization.

The maternal blood sample may be non-treated maternal blood itself. The maternal blood sample may be maternal blood that has been changed by performing some type of chemical or physical process on the original maternal blood so that the changed maternal blood becomes suitable for preservation and efficiency of subsequent processes. Such processes include, for example, adding a preservative such as an apoptosis inhibitor, adjusting a temperature, adding a reagent to prevent precipitation of blood cells, and protecting blood cells from physical damage caused by shaking by using an air cushion. However, the processes are not limited to these examples.

In this embodiment, the maternal blood means blood collected from a pregnant woman. The maternal blood can be collected from a pregnant woman by an ordinary medical method. NRBCs in the collected maternal blood may be concentrated immediately. Further, NRBCs may be concentrated after the maternal blood is transported from a place where the blood is collected to where the blood is concentrated. A desired preservative process may be performed on the maternal blood.

[Nucleated Red Blood Cell (NRBC)]

In this embodiment, an objective is to obtain chromosomal DNA of an NRBC originated from a fetus. NRBCs derived from a fetus are described hereinafter.

In this embodiment, blood cells mean cells in blood. Blood contains blood cells and blood plasma. According to one theory, it is considered that RBCs account for the greater part of human blood cells. Further, WBCs and blood platelets are also included in the blood cells. Maternal blood contains NRBCs derived from a fetus.

In this embodiment, the NRBCs are erythroblasts and preferably erythroblasts that have lost their cell-division ability. RBCs are generated as hematopoietic stem cells differentiate and mature. Through the process of differentiation and maturation, starting from the hematopoietic stem cells, myeloid progenitor cells, RBCs/megakaryocyte precursor cells, prophase erythroid precursor cells (BFU-E), anaphase erythroid precursor cells (CFU-E), proerythroblasts, basophilic erythroblasts, polychromatic erythroblasts, orthochromatic erythroblasts, reticulocytes, and erythrocytes appear one after another.

The erythroblasts include proerythroblasts, basophilic erythroblasts, polychromatic erythroblasts, and normochromatic erythroblasts. Nucleuses are lost from blood cells during the process in which normochromatic erythroblasts differentiate into reticulocytes. In general, normochromatic erythroblasts have already lost their cell-division ability.

NRBCs are usually present in bone marrow. However, as stated in the Background-Art section, a very small amount of NRBCs are found in blood. Further, a very small amount of NRBCs of maternal origin and NRBCs derived from a fetus are found in maternal blood. The number of NRBCs derived from a fetus in maternal blood is usually smaller than the number of NRBCs of maternal origin.

[a. Labeling for Fraction A]

<a-1. Acquisition of Fraction A by Concentration>

In a step a, RBCs and nucleic acids in a fraction A in which NRBCs are concentrated are specifically labeled. Note that fraction A is a fraction obtained by fractionating blood cells in a maternal blood sample based on at least one property of their volumetric mass densities and their sizes. The fraction A may be obtained by fractionating blood cells in a maternal blood sample by both their volumetric mass densities and their sizes. Hereinafter, "a-1. Acquisition of Fraction A by Concentration" and "a-2. Fluorescent Labeling of Fraction A" are separately described.

In a step S21 shown in FIG. 1, a fraction A in which NRBCs are concentrated in a population of whole blood cells, preferably in a population of RBCs, is obtained from a maternal blood sample. In this embodiment, the expression that "NRBCs are concentrated" means that a ratio of NRBCs to the whole blood cells in the fraction is increased. Preferably, it means that a ratio of NRBCs to RBCs is increased.

The acquisition of the fraction A is performed by fractionating blood cells in the maternal blood sample based on their volumetric mass densities or their sizes. The fractionation based on the volumetric mass densities of blood cells may be carried out, for example, by the aforementioned density gradient centrifugation method. The fractionation based on the size of blood cells may be carried out, for example, by a blood-cell separation chip such as the above-described micro-channel chip. By the above-described fractionation, a fraction in which at least some of non-nucleated RBCs have been removed from the blood cells in the maternal blood sample is obtained.

Further, the fractionation based on the size of blood cells may be carried out, for example, by a method using a Dean flow or a Dean force. Such methods may be carried out by using a spiral sorter available from microfluidic chipshop GmbH.

In the step S21 shown in FIG. 1, WBCs may be further removed from the fraction, which is obtained by fractionating the blood cells in the maternal blood sample based on the volumetric mass density or size, by an immunological removal method. In this way, a fraction A in which NRBCs are further concentrated is obtained.

The step S21 shown in FIG. 1 may be incorporated into the below-described steps S22 to S26 and they may be performed as a series of processes in one laboratory. Alternatively, the fraction A may be obtained from maternal blood collected in a clinical facility in that clinical facility and then transported to a central laboratory. In the central laboratory, only the steps S22 to S26 may be performed without performing the step S21.

<a-2. Labeling of Fraction A>

In a step S22 shown in FIG. 1, RBCs and nucleic acids in the fraction A are specifically labeled. The labeling (label or labeling) may be magnetic labeling or fluorescent labeling, though the fluorescent labeling is preferred. The labeling may be direct labeling or indirect labeling. The indirect labeling may be labeling made by a tag and a secondary antibody, or may be labeling made by a biotin-avidin bonding.

The labeling specific to RBCs may be labeling specific to surfaces of RBCs. The labeling specific to RBCs may be immunolabeling. The immunolabeling may be labeling made by an antibody. A target antigen of the immunolabeling may be a carbohydrate antigen. The labeling may be labeling made by an antibody for an antigen specific to RBCs such as CD71 and CD235a (GPA, Glycophorin A).

The immunolabeling specific to RBCs may be labeling specific to premature RBCs. It may be immunolabeling whose target antigen is a peptide chain specific to premature RBCs, such as an embryonic epsilon globin chain of hemoglobin. Such antibodies for immunolabeling are mentioned in Patent Literature 5.

Nuclei contained in NRBCs are specifically labeled by labeling specific to nucleic acids. The labeling specific to nucleic acids may be dye labeling. The nucleic acids to be labeled are preferably DNA. The dye may be a fluorescent dye. Nuclei may be fluorescent-labeled by a fluorescent dye. The fluorescent dye may be Hoechst33342.

Further, an antibody that reacts with a surface antigen present on fetal NRBCs but does not react with a surface antigen present on maternal RBCs may be used. The antibody may be a monoclonal antibody. For example, it may be an antibody 4B9 mentioned in Patent Literature 6. The aforementioned antibodies may be used together with the aforementioned immunolabeling specific to RBCs or the labeling specific to nucleic acids. By using such an antibody, it is possible to perform labeling specific to NRBCs without relying on the labeling specific to nucleic acids.

In the step S22 shown in FIG. 1, the labeling specific to RBCs and the labeling specific to nucleic acids may be performed at the same time. Alternatively, one of the labeling processes may be performed before the other labeling. Further, one of the labeling processes may be performed before the other labeling and the sorting in the step S23 may also be performed before the other labeling. After that, the other labeling and the sorting may be performed.

Note that histological crosslinking-fixing may be performed for blood cells in the fractions A before one or all of the above-described labeling processes may be performed. Further, the below-described fractionation by cell sorting may be performed in this state. It is possible to prevent blood cells from aggregating by crosslinking/fixing blood cells. Therefore, the sorting by cell sorting can be accurately performed. Extracted DNA may be de-crosslinked before a molecular biological analysis is performed in the later-described step d.

The below-described fractionation, i.e., fractionation by cell sorting may be performed without performing histological crosslinking/fixing for blood cells in the fraction A. In this way, it is possible to minimize the effect caused by the crosslinking/fixing in a molecular biological analysis performed in the later-described step d.

For example, labeling specific to nucleic acids and labeling specific to RBCs may be performed at the same time without performing crosslinking/fixing of blood cells. Further, blood cells may be crosslinked/fixed after these labeling processes are performed. Further, immunolabeling specific to WBCs may be performed for crosslinked/fixed blood cells.

[b. Acquisition of Fraction B by Cell Sorting]

<b-1. Basic Cell Selection>

In a step S23, a fraction B is obtained by sorting out labeled blood cells in the fraction A by cell sorting. In the cell sorting, for example, an apparatus used for sorting out cells (e.g., a cell sorter) is used. In the case where the labeling is fluorescent labeling, the sorting method by cell sorting may be a fluorescence activated cell sorting (FACS) method. The sorting method by cell sorting may be a cell sorting method by using magnetic labeling.

In this embodiment, there are no particular limitations on the principle of the cell sorting and the type of the cell sorter. The cell sorting is preferably performed by flow cytometry.

In an aspect, the FACS is performed by a cell analyzer equipped with a sorting apparatus, for example, by a cell sorter. In an aspect, the cell sorter makes cells carried by a continuously-flowing fluid and identifies features of individual cells based on fluorescence of the cells that is generated by irradiating the cells with excitation light. This identification is also a function of the cell analyzer. Based on information obtained by the identification, the cell sorter further confines cells in droplets and collects droplets containing specific cells. By doing so, the cell sorter sorts out the specific cells In an aspect, the cell sorter makes cells carried by a continuously-flowing fluid and identifies features of individual cells based on fluorescence of the cells that is generated by irradiating the cells with excitation light. Based on information obtained by the identification, the cell sorter sorts out fractions containing specific cells in a state in which cells are continuously carried by the continuously-flowing fluid.

As the above-described cell sorter that does not use droplets, a cell sorter that use pulsed flows for the sorting has been known as shown in the later-described FIG. 10 and as disclosed in Patent Literature 7. Further, a cell sorter that uses a sol-gel transition of a fluid for the sorting has been known as disclosed in Patent Literature 8.

In the case of the above-described cell sorter that does not use droplets, since cells can be guided into sorting containers while keeping the cells carried by the fluid, the cells are less likely to be damaged. Further, it is easy to prevent the apparatus and the environment from being contaminated due to splashing of the fluid by confining the fluid in a channel chip during the process for guiding cells to containers.

In a step S23 shown in FIG. 1, blood cells are preferably sorted out so that blood cells that have been labeled with the label specific to RBCs are obtained. Since NRBCs are RBCs, the NRBCs can be distinguished from other blood cells including WBCs by the labeling specific to RBCs.

In the step S23 shown in FIG. 1, the blood cells are preferably sorted out so that blood cells that have been labeled with the label specific to nucleated blood cells are obtained. Since NRBCs have nuclei, the NRBCs can be distinguished from other blood cells including non-nucleated RBCs by the labeling specific to nucleic acids.

In the step S23 shown in FIG. 1, a fraction B having increased purity of NRBCs is obtained by combining the above-described labeling processes. The obtained fraction B includes NRBCs of maternal origin and NRBCs derived from a fetus. The sorting by the labeling specific to RBCs and the sorting by the labeling specific to nucleic acids may be performed at the same time. Alternatively, one of the sorting processes may be performed before the other sorting. For example, a fraction B may be obtained by first performing sorting by magnetic labeling specific to RBCs and then performing sorting by using fluorescent labeling specific to nucleic acids.

In the step S22 shown in FIG. 1, WBCs in the fraction A may be specifically labeled in an additional manner. The labeling specific to WBCs may be immunolabeling. This labeling may be labeling for an antigen specific to WBCs such as CD45. The antigen may be a carbohydrate antigen. In the step S23, blood cells are preferably sorted so that blood cells that have been labeled with the WBCs specific label are removed.

<b-2. Additional Cell Selection>

In the step S21 shown in FIG. 1, when blood cells in the fraction A are fluorescent-labeled, the FACS is preferably used as the cell sorting. Further, since the fluorescent label remains even after the cell-sorting process, this fluorescent label may be effectively used.

For example, cells may be further sorted out by additionally using fluorescence for the first fraction obtained by the cell sorting. For example, the second and subsequent fractions may be obtained by further repeating the sorting by the cell sorting for the obtained first fraction. In this way, the aforementioned fraction B may be eventually obtained.

[c. Separation of Blood Cell and DNA Extraction]

In a step c, each of blood cells in the fraction B is separated at a single-cell level. Further, a process for extracting chromosomal DNA is independently performed for each of the separated blood cells. In this way, fractions C each of which contains chromosomal DNA distinguishable at a single-cell level are obtained. In this embodiment, the chromosomal DNA means a genomic DNA.

Hereinafter, "c-1. Separation of Blood Cell at Single-Cell Level" and "c-2. Acquisition of Fraction C by DNA Extraction" are separately described.

<c-1. Separation of Blood Cell at Single-Cell Level>

In a step S24 shown in FIG. 1, each of blood cells in the fraction B is separated at a single-cell level. Further, blood cells in fraction B are separated from each other at a single-cell level. In this embodiment, the separation of blood cells at a single-cell level includes separating blood cells on a cell-by-cell basis. That is, it includes obtaining a single cell.

The separation of blood cells in the fraction B at a single-cell level is preferably performed indiscriminately irrespective of whether or not each of the blood cells in the fraction B has a characteristic of an NRBC. That is, blood cells are preferably separated irrespective of whether or not each blood cell is an NRBC. The term "indiscriminately" is not intended to eliminate concentrations of NRBCs based on their volumetric mass densities and their sizes, and based on their labeling in the processes up to the acquisition of the fraction B.

Figure 2:
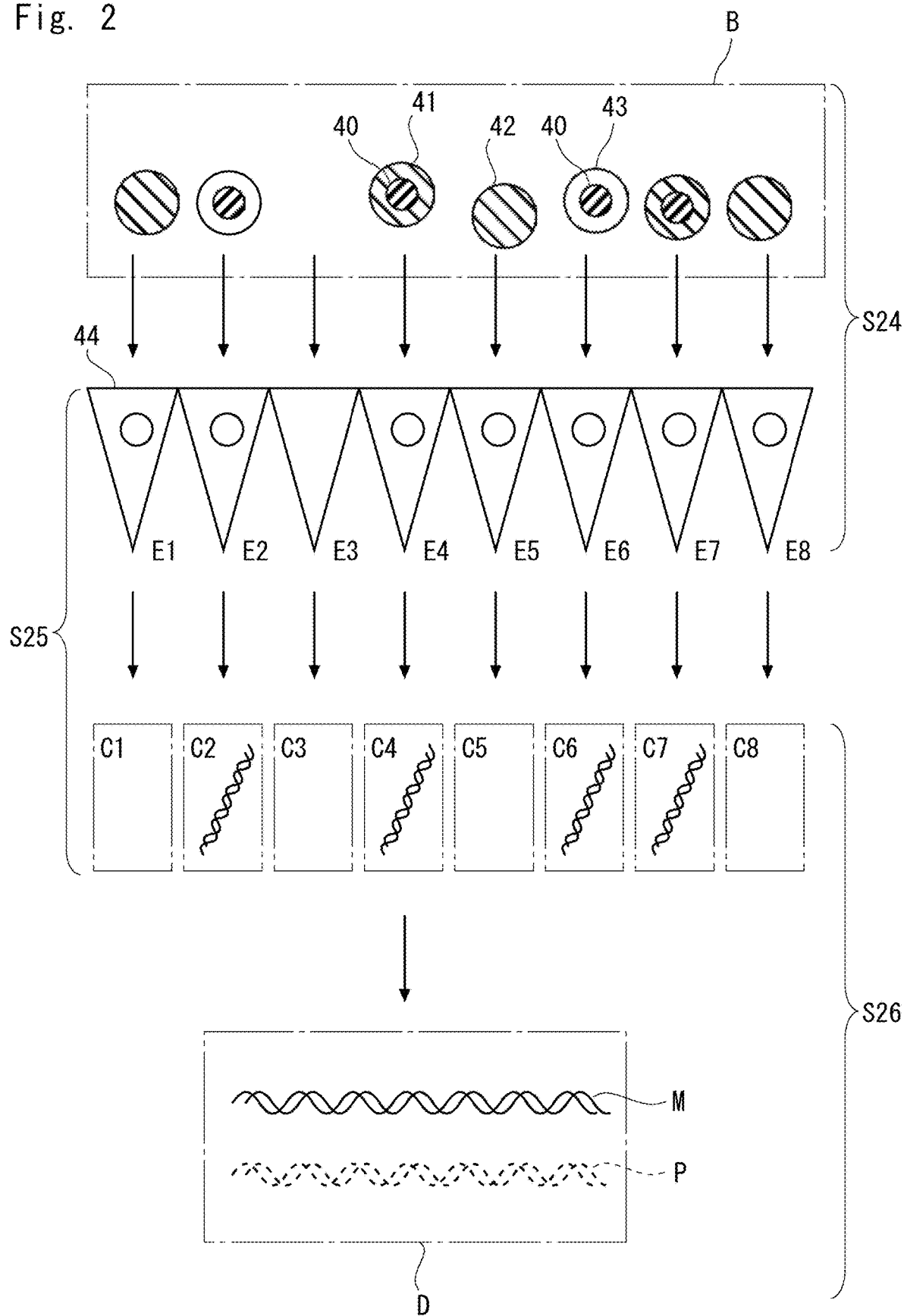
FIG. 2 is a conceptual diagram showing a separation at a single-cell level and a DNA extraction.

As a result of the above-described concentration and the cell sorting, NRBCs 41 containing cell nuclei 40 are contained in relatively abundance in the fractions B shown in FIG. 2. The fraction B may also contain other blood cells. The other blood cells include, for example, non-nucleated RBCs 42 and WBCs 43 containing cell nuclei 40. The indiscriminate separation means separating these cells at a single-cell level in an all-inclusive manner.

Each of blood cells in the fraction B shown in FIG. 2 is preferably distributed to an individual container 44 in order to separate them at a single-cell level. By this distribution, the fraction B can be further fractionated. The fractionation is preferably performed by a limited dilution method. By performing the fractionation by the limited dilution method, fractions E each of which contains a blood cell separated at a single-cell level can be obtained. The limited dilution method may be performed, after a sorting volume is defined so that the number of obtained fractions becomes larger than the number of blood cells, by sorting out blood cells from a well-suspended fraction B.

In FIG. 2, eight containers each of which is equivalent to the container 44 are shown in total. The number of containers 44 can be determined as desired according to the number of blood cells in the fraction B or the number of fractions C to be obtained. For example, the containers may be eight-tubes, or may be a well plate with 96 holes, 384 holes, or any number of holes. In FIG. 2, fractions E1, E2, and E4-E8 are shown as the fractions E. In the limited dilution method, a fraction(s) that contains no blood cell may be generated as in the case of the fraction E3.

The distribution of blood cells into the containers 44 shown in FIG. 2 is preferably performed indiscriminately as described above. That is, the distribution of NRBCs 41 does not eliminate at all distributions of non-nucleated RBCs 42 and WBCs 43 at a single-cell level.

This embodiment does not rely on the discrimination of candidate cells for fetal NRBCs based on morphological information of cells as described, for example, in Patent Literature 4. Further, this embodiment does not include isolating candidate cells on a cell-by-cell basis based on such discrimination of candidate cells. In the separation at a single-cell level in this embodiment, it is preferred that such an isolation operation including identification of NRBCs be not performed. In a preferred aspect, the method according to this embodiment does not include an additional process for sorting out blood cells from a fraction based on morphological information of blood cells that is performed before a fraction obtained by cell sorting is processed in a process for separating blood cells at a single-cell level in the step c-1.

In this embodiment, it is preferable to use a limited processing time preferentially for the separation of blood cells at a single-cell level. In a preferred aspect, the method according to this embodiment does not include the above-described process for distributing a fraction on a planar chip and identifying NRBCs by fluorescence. In a preferred aspect, the method according to this embodiment does not include an additional process for sorting out blood cells from a fraction B that is performed before a fraction obtained by cell sorting is processed in a process for separating blood cells at a single-cell level in the step c-1.

The above description does not eliminate observing a part of or the whole fraction A or the fraction B and confirming that NRBCs are contained therein. For example, quality of each process may be controlled by observing a part of a fraction by a microscope and confirming the presence of NRBCs by information based on morphological information or fluorescence, or information based on other characteristics.

Figure 3:
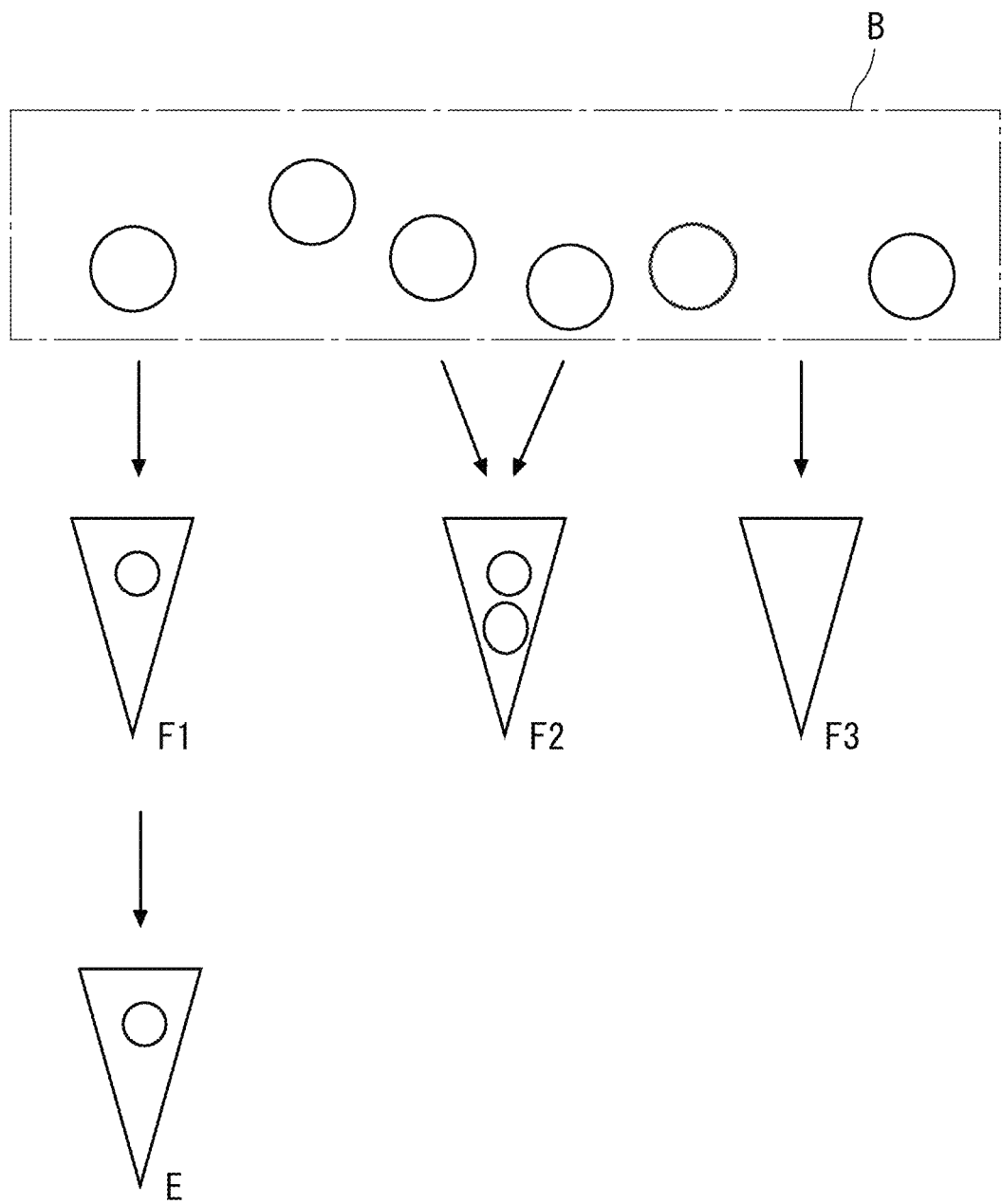
FIG. 3 is a conceptual diagram showing a limited dilution method.

FIG. 3 shows a type of a limited dilution method. In this method, fractions F are indiscriminately sorted out from a fraction B. That is, the fractions F are sorted out irrespective of whether or not each blood cell is an NRBC. In the figure, fractions F1 to F3 are shown as the fractions F. These fractions F1 to F3 are photographed. The fraction F1 contains a blood cell separated at a single-cell level. The fraction F2 contains two cell blood cells. The fraction F3 contains no blood cell. They are confirmed by using images of the fractions F1 to F3. As a result, the fraction F1 is obtained as a fraction E. Alternatively, it may be determined whether or not a fraction E has been obtained through an image analysis. The fraction F2 may be returned to the fraction B.

In the limited dilution method shown in FIG. 3, it is possible to determine whether or not one cell has actually been dispensed when each fraction is dispensed by using a camera or the like. By this method, blood cells can be separated at a single-cell level more reliably. Further, it is possible to avoid generation of a fraction containing no blood cell. A single-cell dispenser "On-chip SPiS" available from On-chip Biotechnologies Co., Ltd. may be used to carry out the above-described limited dilution method.

Further, the step S24 shown in FIG. 1 may be carried out by dispersing blood cells of the fraction B on a slide or a chip and then indiscriminately isolating these blood cells one by one. That is, the blood cells are isolated irrespective of whether or not each blood cell is an NRBC. Further, the step S24 may be performed while performing the cell sorting in the step S23, i.e., performed in parallel with the cell sorting in the step S23. That is, in the cell sorting, very small amounts of fluids containing blood cells are successively sorted out. These fluids may be dispensed into separate containers without collecting the fluids into one container again so that each container contains one blood cell.

<c-2. Acquisition of Fraction C by DNA Extraction>

In a step S25 shown in FIGS. 1 and 2, fractions C are obtained by independently performing a process for extracting chromosomal DNA for each of separated blood cells. By performing the steps S24 and S25, each of the fractions C contains chromosomal DNA distinguishable at a single-cell level. In this embodiment, the fraction containing chromosomal DNA capable for tracing back it to a blood cell before chromosomal-DNA extraction at a single-cell level includes a fraction containing chromosomal-DNA extracted from a single blood cell.

As shown in FIG. 2, it is preferable to indiscriminately perform a process for extracting chromosomal DNA for the fractions E1 to E8 containing blood cells sorted out into individual containers 44. The extraction process is indiscriminately performed irrespective of whether or not each of blood cells contained in the fraction B has a characteristic of an NRBC. Further, the extraction process is indiscriminately performed irrespective of whether or not a blood cell contained in each of the fractions E has a characteristic of an NRBC. That is, the extraction process is performed irrespective of whether or not each blood cell is an NRBC. The term "indiscriminately" is not intended to eliminate concentrations of NRBCs based on their volumetric mass densities and their sizes, and based on their labeling in the processes up to the acquisition of the fraction B.

As a result of the extraction process, fractions C1, C2 and C4-C8 are obtained as the fractions C. That is, the extraction of chromosomal DNA from NRBCs 41 does not eliminate at all extractions of chromosomal DNA from non-nucleated RBCs 42 and WBCs 43. Further, there may be a fraction that is obtained by performing a chemical process for extracting chromosomal DNA for a fraction containing no blood cells as in the case of the fraction C3.

The DNA extraction process is independently performed at a single-cell level. Therefore, for example, chromosomal DNA derived from NRBCs 41 are contained in the fractions C4 and C7. Further, chromosomal DNA of other cells are not mixed in the fractions C4 and C7. As described above, chromosomal DNA having purity equivalent to that of chromosomal DNA obtained from NRBCs that are isolated in advance are contained in the fractions C4 and C7. Note that regarding the purity mentioned here, attention is paid to the presence or absence of mixing of chromosomal DNA of WBCs of maternal origin.

As shown in FIG. 2, the extractions of chromosomal DNA are indiscriminately performed for individual blood cells. That is, the extraction process is performed irrespective of whether or not each blood cell is an NRBC. As a result, no chromosomal DNA is contained in the fractions C1, C5 and C8 derived from non-nucleated RBCs 42. Chromosomal DNA of WBCs are contained in the fractions C2 and C6 derived from WBCs 43. Since there was no blood cell in the fraction E3, no chromosomal DNA is contained in the fraction C3.

The method according to this embodiment allows for the above-described inefficient operations. By indiscriminately separating cells and extracting DNA as described above, chromosomal DNA of NRBCs can be obtained without relying on the isolation operation including identification of NRBCs. Therefore, the overall efficiency of the series of processes is improved.

In the step c in this embodiment, the following three points should be noted. As the first point, for a person who carries out this embodiment, it is acceptable that the fact that chromosomal DNA derived from NRBCs are contained in the fractions C4 and C7 among the eight fractions C shown in FIG. 2 is still unknown in the step c. This is because it is not essential to isolate NRBCs based on morphological information in the method according to this embodiment. More specifically, this is because the fractions C are indiscriminately obtained as described above.

As the second point, it is presumed that chromosomal DNA derived from an NRBC was obtained in one of the fractions C shown in FIG. 2 in an after-the-fact manner by performing a molecular biological analysis in the later-described step d. In general, fetal cells mixed in maternal blood are fetal NRBCs. Therefore, the above-described presumption is made when it is found out that the chromosomal DNA is derived from a fetus.

As the third point, for a person who carries out this embodiment, it is acceptable that whether chromosomal DNA contained in the fractions C4 and C7 shown in FIG. 2 are derived from NRBCs of the mother or derived from fetal NRBCs is still unknown in the step c. This is because it is not essential to use means for distinguishing NRBCs of the mother from fetal NRBCs in the aforementioned step. The fact that the chromosomal DNA is derived from a fetus is found out in an after-the-fact manner by performing a molecular biological analysis in the later-described step d.

Figure 4:
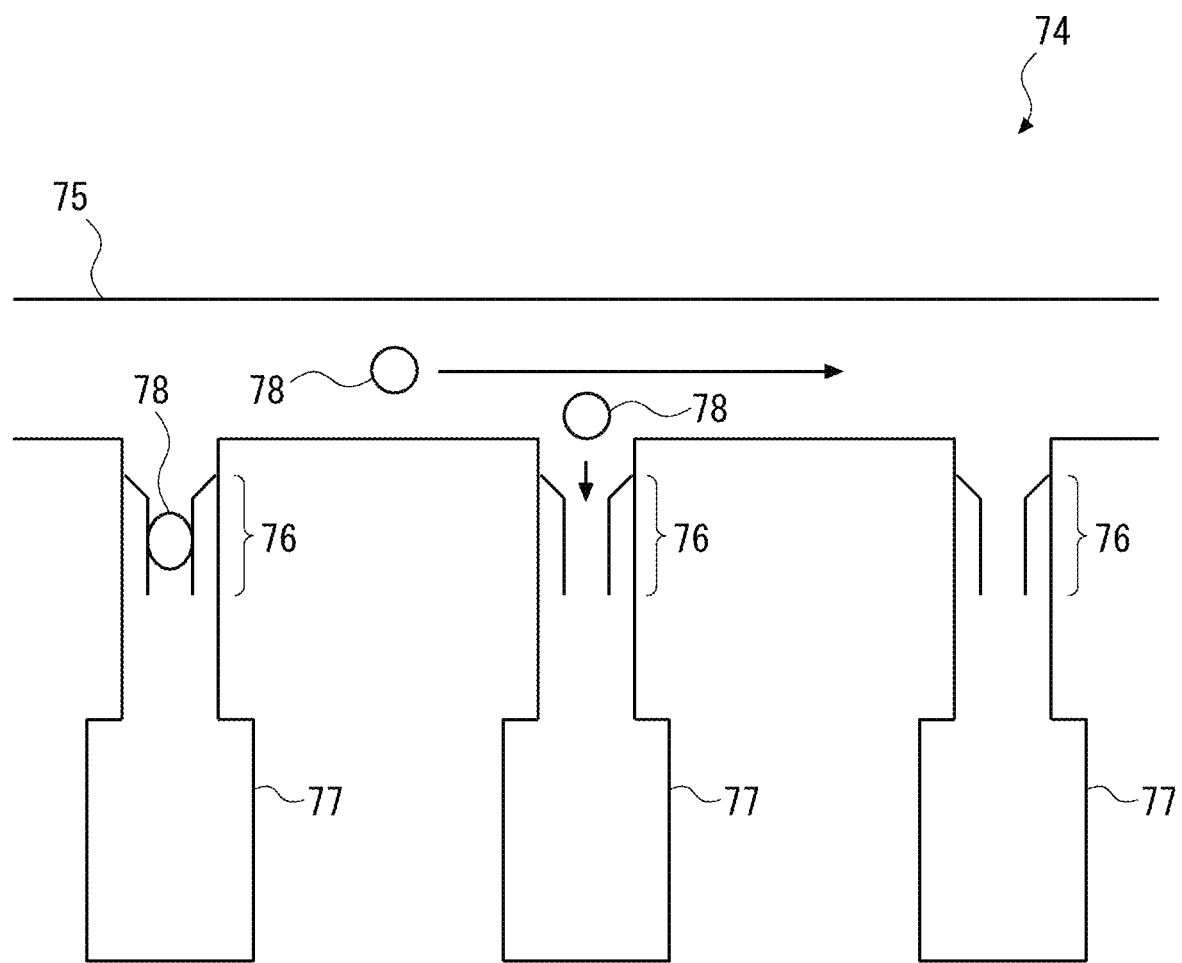
FIG. 4 is a schematic diagram of an apparatus that separate cells at a single-cell level.

An apparatus 74 shown in FIG. 4 may be used in place of the containers 44 shown in FIG. 2. The apparatus 74 includes a channel 75, trapping structures 76, and reaction structures 77. A plurality of trapping structures 76 are successively arranged along the channel 75. The reaction structures 77 are provided for the respective trapping structures 76.

In the apparatus 74 shown in FIG. 4, cells 78 are distributed into each trapping structure 76 and hence the cells 78 are separated from each other at a single-cell level. However, cells 78 trapped by the trapping structures 76 are not sorted out into specific containers. After all the cells 78 or a desired number of cells 78 are trapped in the trapping structures 76, the trapped cells 78 are dissolved and the cells are processed by washing out the dissolved substance toward the reaction structures 77. In the reaction structures 77, extractions of chromosomal DNA and the below-described reaction for whole genome amplification may be performed as the processes for cells.

As the apparatus 74 shown in FIG. 4, a micro-fluid device disclosed in Patent Literature 9 may be used. Further, as the micro-fluid device, C1 Single-Cell Auto Prep Array IFC available from Fluidigm Corporation may be used.

[d. Selection of Fraction D from Group of Fractions C]
<d-1. Selection of Fraction D by DNA Analysis>

In a step S26 shown in FIGS. 1 and 2, a molecular biological analysis is performed for each of the fractions C. By doing so, a fraction D containing chromosomal DNA derived from a fetus is selected from the group of fractions C. As shown in FIG. 2, the fraction D contains a copy of DNA of a chromosome P of father origin in addition to a copy of DNA of a chromosome M of mother origin. When the fetus is male, a Y-chromosome is paired with an X-chromosome, but they are not homologous chromosomes.

Figure 5:
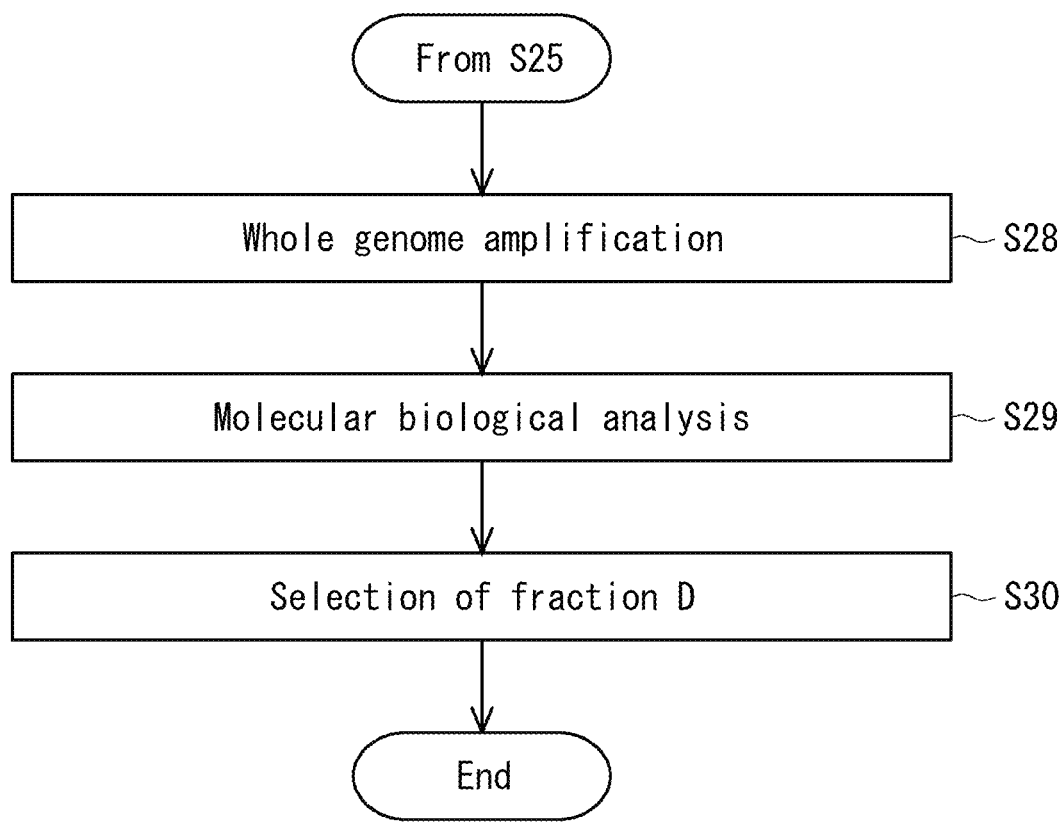
FIG. 5 is a flowchart for a selection of a fraction D.

FIG. 5 shows a preferred example of the step S26 shown in FIGS. 1 and 2. In a step S28 shown in FIG. 5, whole genome amplification is performed for the chromosomal DNA in the fraction C. As a method for the whole genome amplification, a PCR method typified by MALBAC (Multiple Annealing and Looping Based Amplification Cycles), MDA (Multiple Strand Displacement Amplification), and DOP-PCR (Degenerate oligonucleotide-primed PCR) can be used. Among them, the MALBAC is preferred because unevenness in amplification is small over the entire area of the genome.

By the whole genome amplification, copies of the chromosomal DNA are contained in abundance in the fraction C. Hereinafter, copies of chromosomal DNA are also referred to as chromosomal DNA, unless otherwise specified.

In a step S29 shown in FIG. 5, a molecular biological analysis is performed. In this way, it is distinguished whether chromosomal DNA in each fraction C is of maternal origin or derived from a fetus. In the distinction, the following points may be noted.

In this embodiment, chromosomes of maternal origin are distinguished from chromosomes of mother origin. The chromosomes of maternal origin are exclusively derived from somatic cells of the mother's body. In the case of a pair of chromosomes of maternal origin, both the chromosomes in the pair are derived from the mother's body.

In this embodiment, chromosomes of mother origin mean chromosomes derived from reproductive cells of the mother. Chromosomes of mother origin mean chromosomes derived from a fetus, unless otherwise specified. These chromosomes form homologous chromosomes with chromosomes of father origin.

When the mother's body is the same as the mother, a DNA sequence of a chromosome of mother origin is the same as a DNA sequence of a chromosome of maternal origin. Note that the method according to this embodiment can be applied even when the fetus is derived from an egg derived from a woman other than the mother, instead of being derived from an egg of the mother's body.

An STR (Short tandem repeat) analysis is preferred as the molecular biological analysis in the step S29 shown in FIG. 5. The STR (Short Tandem Repeat) analysis makes it possible to distinguish between a sequence of father origin and a sequence of mother origin. DNA derived from a fetus contains an STR that is not of mother origin. Therefore, it is possible to identify that chromosomal DNA is derived from a fetus irrespective of the sex of the fetus.

When it is already determined that the fetus is male, an analysis based on a sequence specific to a Y chromosome may be performed. DNA derived from a male fetus contains a Y chromosome that is not derived from the mother. Therefore, it is possible to identify that the chromosomal DNA is derived from a fetus.

In a step S30 shown in FIG. 5, it is checked which of the fractions C is derived from the fetus based on the result of the above-described molecular biological analysis. In this way, it is possible to select a fraction D from the fractions C.

In the step S30 shown in FIG. 5, it is not essential to confirm that the fraction D is derived from an NRBC without doubt. In the step S30, the morphological information of the blood cell has already been lost. Since the purity of NRBCs is increased in the step S23, it is stochastically presumed that the fraction D was originated from an NRBC.

Figure 6:
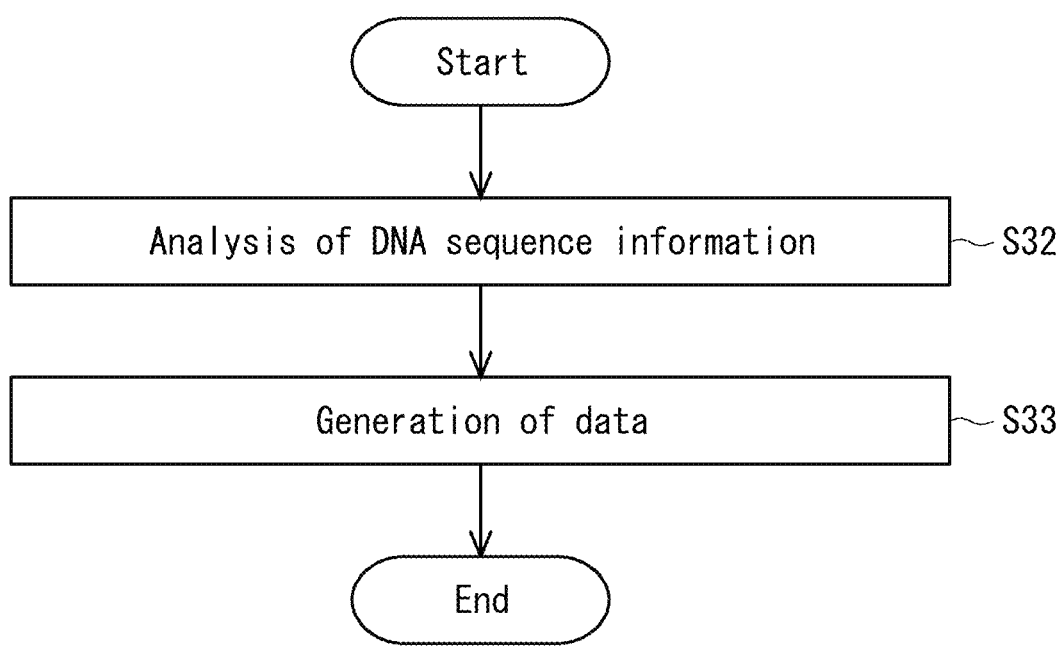
FIG. 6 is a flowchart for an acquisition of diagnostic data.

Through the series of processes shown in FIGS. 1 to 5, it is possible to obtain a fraction D containing chromosomal DNA derived from an NRBC originated from a fetus isolated at a single-cell level. In order to use this chromosomal DNA for a prenatal diagnosis, processes shown in FIG. 6 are performed.

Note that in general, the terms "prenatal testing" and "prenatal diagnosis" may include non-definitive testing. Further, chromosomal DNA obtained by this embodiment may be used for a definitive diagnosis. This is because data for testing obtained in this embodiment is obtained solely from chromosomal DNA in a fetal cell.

The effect on data obtained by using only chromosomal DNA derived from a fetus caused by mixing of chromosomal DNA of maternal-cell origin in a DNA sample is extremely small or is not caused at all. Note that the presence or absence of mixing mentioned here does not mean the principle of heredity, i.e., the principle that a half of a homologous chromosome of a fetus is derived from the mother and the other half is derived from the father.

It is considered that the method according to this embodiment is more suitable for a definitive diagnosis than conventional NIPT, such as one using DNA fragment contained in plasma, is. This is because chromosomal DNA of maternal-cell origin and chromosomal DNA of fetal cell origin are mixed in a DNA sample used in the conventional NIPT.

The above-described chromosomal DNA and data obtained in this embodiment may be used for an NIPD (Non-invasive prenatal diagnosis). A doctor can determine whether or not chromosomal DNA or data in this embodiment is used for non-definitive testing or a definitive diagnosis. The adequacy as to whether or not a diagnosis based on chromosomal DNA and data obtained by this embodiment is used as a definitive diagnosis depends on a medical judgment and does not affect the technical essence of the present invention.

When DNA is analyzed, it is necessary to unlink cross-linking that was used for fixing of chromosomal DNA. That is, the chromosomal DNA is de-crosslinked. By doing so, it is possible to efficiently proceed with the DNA analysis. Further, the crosslinking may be omitted, so that the DNA is prevented from being damaged in the de-crosslinking reaction.

[e. Acquisition of Data Used for Diagnosis]

<e-1. Acquisition of Data Used for Diagnosis Using Chromosomal DNA as Sample>

FIG. 6 shows a method for obtaining data used for a diagnosis. In a step S32, part or all of sequence information of chromosomal DNA of the above-described fraction D is analyzed. The analysis may be performed by using sequencing. The sequencing may be performed on a part of or the whole genome. The sequencing may be Sanger sequencing or NGS (Next generation sequencing).

The NGS may be any of pyrosequencing provided by F. Hoffmann-La Roche Ltd; sequencing by synthesis provided by Illumina Inc.; and sequencing by ligation and ion semiconductor sequencing provided by Thermo Fisher SCIENTIFIC Inc.

In the step S32 shown in FIG. 6, the analysis of sequence information may be performed by using a micro-array. The micro-array may be an SNP micro-array. In the method according to this embodiment, copies can be obtained without causing unevenness in the number of copies over the entire length of chromosomal DNA derived from a fetus. Therefore, it is suitable for providing reliable SNP micro-array data, which is difficult to be obtained in the MPS (Massive parallel sequencing) method. Further, the micro-array may be a CGH array.

In a step S33 shown in FIG. 6, data that is suitable for a diagnosis made by a doctor is generated from the analysis result of the sequence information. This data may include part of or the whole analyzed raw data. Further, data suitable for a medical statistical analysis may be created under legitimate procedures.

Modified Example

Note that the present invention is not limited to the above-described embodiments and can be modified as appropriate without departing from the spirit and scope of the present invention. The above-described embodiment is a method for human beings. The method according to this embodiment may be applied to mammals other than human beings.

<Hemolytic Method>

In the above-described embodiment, the volumetric mass density or the size of blood cells in a maternal blood sample is used to remove at least some of non-nucleated RBCs from the blood cells. Non-nucleated RBCs may be selectively removed by selectively hemolyzing blood cells in the maternal blood sample. In this way, hemolyzed non-nucleated RBCs are excluded from the range of all the blood cells in the fraction. Therefore, it is possible to obtain a fraction A in which NRBCs are concentrated. The hemolysis can be performed, for example, by adjusting an osmotic pressure of a dispersion medium in which blood cells are dispersed by using an ammonium chloride hemolytic agent.

<Sorting by Planar Chip>

Figure 7:
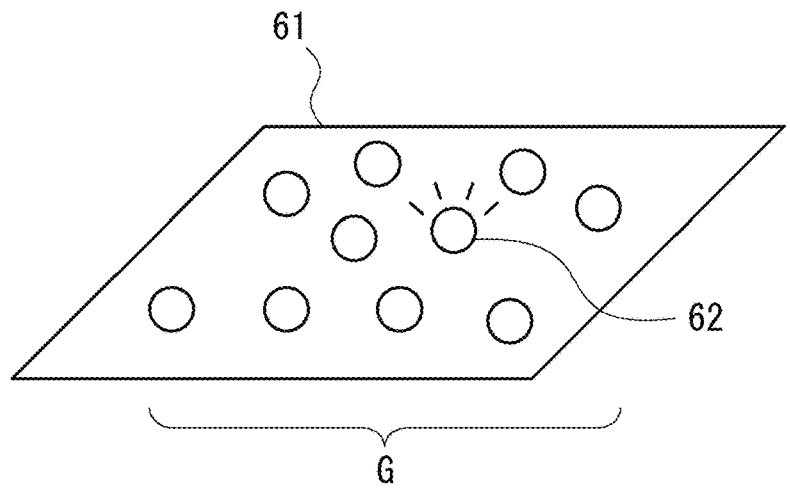
FIG. 7 is a schematic diagram showing sorting performed by fluorescence on a planar chip.

FIG. 7 is a schematic diagram of sorting performed by fluorescence on a planar chip. As described above, a fraction B is obtained by cell sorting in the step S23 shown in FIG. 1. Note that as another fractionation method for assisting the sorting by cell sorting, a sorting method using a planar chip may be additionally used.

Firstly, a fraction G having increased purity of nucleated red blood is obtained by sorting out fluorescent-labeled blood cells in the fraction A by cell sorting as described above. After that, blood cells in the fraction G are spread on a planar chip 61 as shown in FIG. 7. Further, blood cells 62 that emit signals of the labels specific to RBCs and nucleic acids are sorted out from the planar chip 61. In this way, a fraction B having purity of NRBCs further increased from the purity of the fraction G is obtained.

As the above-described fluorescent-sorting means by using a planar chip, DEPArray available from Menarini Silicon Biosystems (Patent Literature 10), and CyteFinder and CytePicker available from RareCyte, Inc. may be used.

As described above, the method according to this embodiment does not rely on the precise determination as to whether or not blood cells are NRBCs made by the sorting means using a planar chip. Note that in some cases, it is possible to carry out the acquisition of the fraction B and the acquisition of the fraction C through a unified process by using the aforementioned apparatuses.

Example 1

<Collecting Blood>

Figure 8:
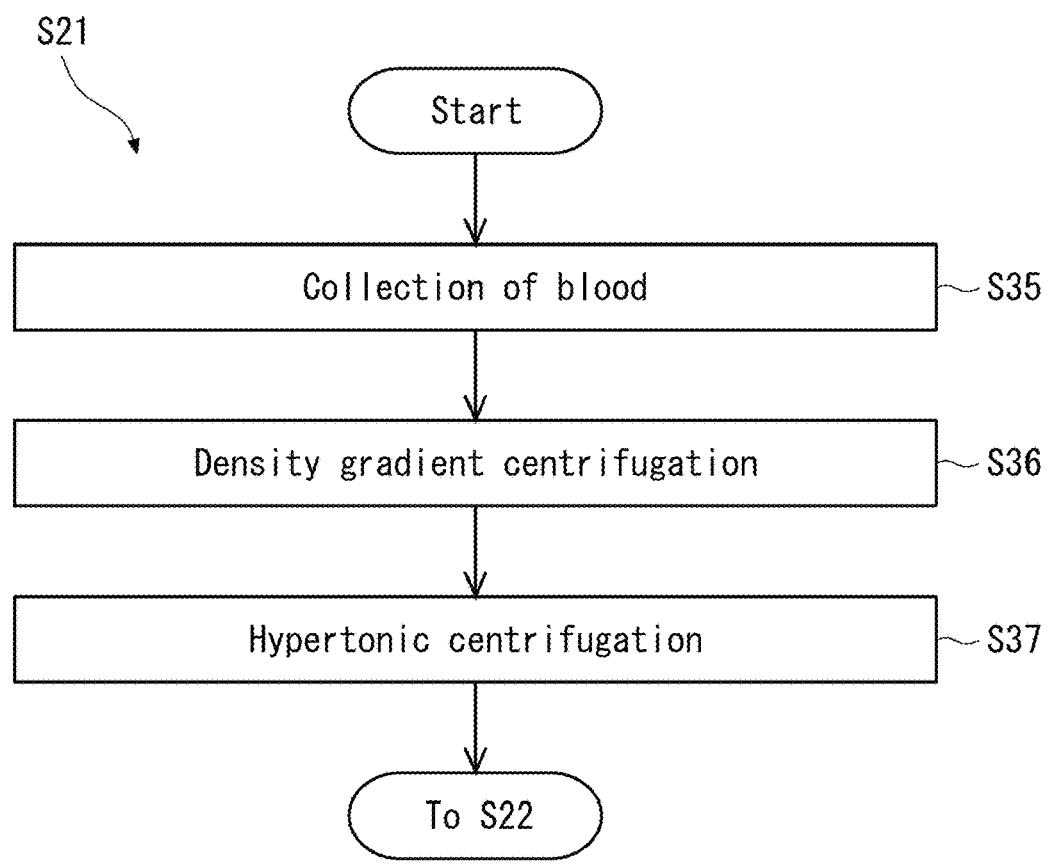
FIG. 8 is a flowchart for an obtaining of a fraction A.

FIG. 8 shows an example of the step S21 shown in FIG. 1. In a step S35, maternal blood is collected. In this example, maternal blood and ordinary blood are obtained under legitimate procedures. The maternal blood was provided by a pregnant woman in 33th week of pregnancy for testing and research. The sex of the fetus was male. The ordinary blood used in this example was provided by a person who was not pregnant for testing and research. The maternal blood and the ordinary blood were collected in medical institutions (facilities). These blood samples were transported to a laboratory of the inventor et al. under appropriate management.

An amount of necessary maternal blood is considered as follows. In general, it is known that about $3 \times 10^{10}$ blood cells are contained in 10 ml of maternal blood. Further, it is known that about 36 to 2168 NRBCs are contained in maternal blood having the same volume (Non-patent Literature 1).

In view of the above-described ratio of NRBCs, an amount of maternal blood used as a starting material may be 0.01 to 100 ml. The amount of the maternal blood may be 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 30, 40, 50, 60, 70, 80 or 90 ml. In this example, 20 ml of maternal blood was used as a starting material.

According to measurement by a fully-automatic cell counter TC20 (BIORAD), $3.16 \times 10^{10}$ blood cells were contained in every 10 ml of maternal blood. The maternal blood was diluted with the same volume of PBS (phosphate buffered saline).

The subsequent concentration process by a density gradient centrifugation method is performed preferably within 48 hours or 36 hours, and more preferably within 24 hours, further preferably within 3 hours, and particularly preferably within 2 hours after the collection of blood. The shorter the time period from the collection of blood to the start of the process is, the more the efficiency of the concentration by the density gradient centrifugation method can be improved. In this example, the process was started two hours after the collection of blood. Further, it is possible to prevent the efficiency of the concentration from deteriorating due to the elapse of time by adding a preservative such as an apoptosis inhibitor.

<Concentration of NRBC>

Through steps S36 and S37 shown in FIG. 8, NRBCs in the maternal blood are concentrated by a density gradient centrifugation method including two stages. Note that the concentration means removing blood cells other than NRBCs. The blood cells that are removed from the maternal blood during the concentration are preferably non-nucleated RBCs. More preferably, platelets are also removed from the maternal blood during the concentration.

A fraction A is obtained by the concentration performed through the steps S36 and S37 shown in FIG. 8. After the concentration, a ratio of NRBCs to all the blood cells in the fraction A is higher than a ratio of NRBCs to all the blood cells in the maternal blood sample.

In the step S36 shown in FIG. 8, the maternal blood is fractionated by a density gradient layered centrifugation method. The density gradient layered centrifugation method is a type of the density gradient centrifugation method. In this example, isotonic solutions having densities of 1.085 g/ml and 1.075 g/ml were prepared by using percoll and saline. After stacking them one by one in a centrifuge tube, 10 ml of maternal blood was further layered. The centrifuge tube was centrifuged with 1,750 G at 20° C. for 30 minutes.

Figure 9:
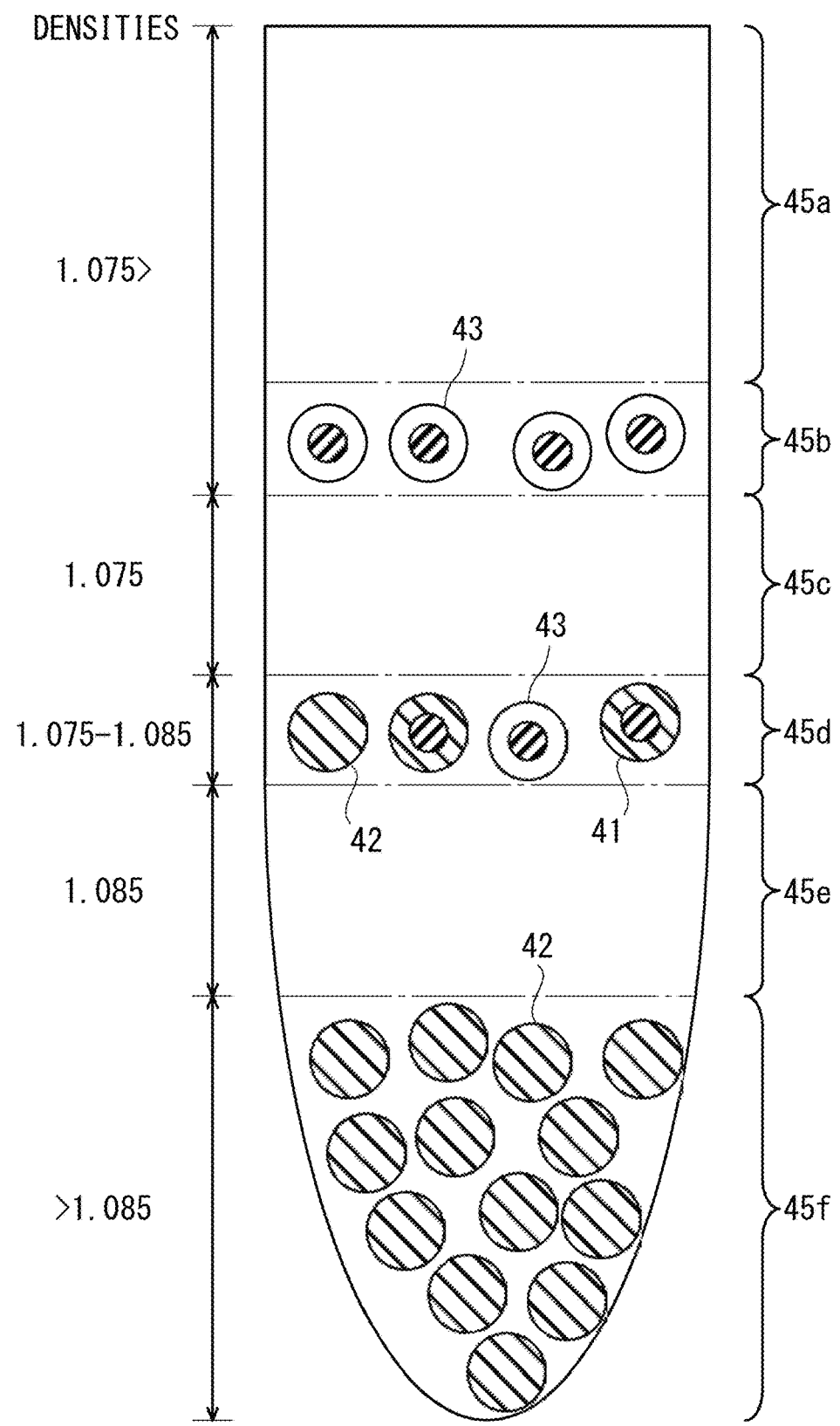
FIG. 9 is a schematic view showing a result of a density gradient centrifugation for maternal blood.

FIG. 9 shows a schematic diagram showing a result of the density gradient layered centrifugation. From the top of the centrifugal tube 46, layers 45*a* to 45*f* are formed one after another. Plasma is concentrated in the layer 45*a*. WBCs 43 are concentrated in the layer 45*b*. It is presumed that the densities of the layers 45*a* and 45*b* are smaller than 1.075 g/ml. The layer 45*c* is a layer of an isotonic solution having a density of 1.075 g/ml.

NRBCs 41 are concentrated in the layer 45*d* shown in FIG. 9. It is presumed that the density of the layer 45*d* is larger than 1.075 g/ml and smaller than 1.085 g/ml. A fraction containing NRBCs was obtained by sorting out blood cells from the layer 45*d* and washing the blood cells. This fraction was referred to as a sample 1. The number of blood cells in the sample 1 was measured by using a fully-automatic cell counter TC20. The number of blood cells was about $9.95 \times 10^{6}$.

The layer 45*e* shown in FIG. 9 is a layer of an isotonic solution having a density of 1.085 g/ml. Non-nucleated RBCs 42 are concentrated in the layer 45*f*. It is presumed that the density of layer 45*f* is larger than 1.085 g/ml.

In the step S37 shown in FIG. 8, the fraction obtained in the step S36 may be fractionated by hypertonic centrifugation (Patent Literature 1). The hypertonic centrifugation is a type of the density gradient centrifugation method. Next, a half of the sample 1 was used as a fraction A and the following step for fluorescent labeling was performed.

<Fluorescent Labeling>

In a step S22 shown in FIG. 1, blood cells in the fraction A are fluorescent-labeled. It is preferable that fluorescent-labeled blood cells are separated from other blood cells including the fluorescent-labeled blood cells. In this example, the fluorescent-labeling can be performed, for example, under the following conditions.

Firstly, blood cells in the fraction A were simultaneously stained with Hoechst33342 (manufactured by Sigma-Aldrich), an anti-CD45-PE labeled antibody (manufactured by Miltenyi-Biotec, clone name: 5B1), and an anti-CD235a-FITC labeled antibody (Miltenyi-Biotec, clone Name: REA175). Crosslinking/fixing of blood cells was not performed in the staining process. The staining was performed at 4° C. for 10 minutes. After the staining, labeled blood cells were collected by centrifuging a suspension of blood cells with 300 G at 4° C. for 10 minutes.

Note that the conditions for the fluorescent labeling may be changed as follows. For example, firstly, blood cells of the fraction A may be stained with Hoechst33342. After that, blood cells may be immune-stained with an anti-CD45-PE labeled antibody and an anti-CD235a-FITC labeled antibody. An antibody-antigen reaction may be advanced at a room temperature while inversion-mixing the blood cells and the antibodies. After that, phosphate buffered saline may be added in the suspension of blood cells. By doing so, the concentration of the added fluorescent antibody can be lowered. After that, blood cells may be collected by centrifuging the suspension of blood cells with 300 g at 25° C. for three minutes.

The concentration of the antibody may be about $1/100$ to $1/10$ of the normal concentration of the antibody mentioned in a document attached to the antibody. In this way, it is possible to improve a signal/noise ratio in the cell sorting process. In this example, regarding the dilution of the antibody, a volume ratio (i.e., a dilution ratio) between the anti-CD45-PE labeled antibody and the buffer solution was 1:10. Further, a volume ratio (i.e., a dilution ratio) between the anti-CD235a-FITC labeled antibody and the buffer solution was 1:1099.

In a step S23 shown in FIG. 1, the fraction A is further fractionated by cell sorting. As a cell sorter, a cell sorter shown in a schematic diagram of FIG. 10 was used. This cell sorter is used to detect fluorescence of blood cells.

Figure 10:
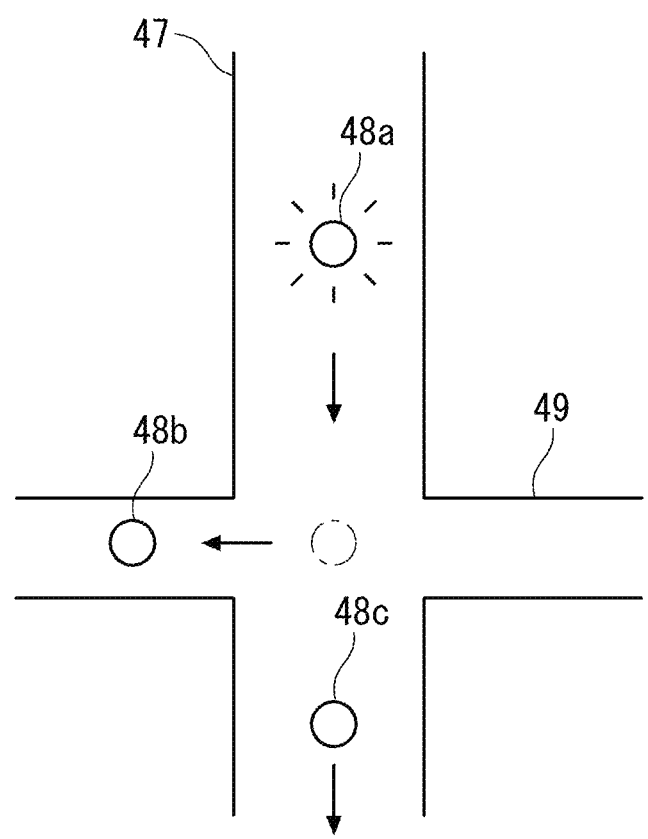
FIG. 10 is a schematic diagram of a cell sorter.

Firstly, a steady liquid flow containing the fluorescent-labeled fraction A is generated in a main channel 47 shown in FIG. 10. Excitation light is applied to a blood cell 48*a* in the liquid flow and the presence or absence of a signal of the label is detected based on fluorescence. A sub channel 49 intersects the main channel 47. The blood cell 48a flows toward the intersection between the main channel 47 and the sub channel 49.

A blood cell 48b shown in FIG. 10 is a blood cell for which the signal is detected. This blood cell flows through the main channel 47 and enters the intersection. In the sub channel 49, a pulsed flow can be generated in a direction intersecting the liquid flow. Based on the aforementioned signal, a pulsed flow is generated with the blood cell 48b being its target.

By making the blood cell 48b shown in FIG. 10 carried by the pulsed flow through the sub channel 49, the blood cell 48b is separated from the liquid flow through the main channel 47. Separated blood cells 48b are successively collected. In this way, a fraction B composed of collected blood cells 48b is generated.

In FIG. 10, no pulsed flow is generated for a blood cell 48c for which no signal is detected or the signal is weak. The blood cell 48c is continuously carried by the liquid flow and flows through the main channel 47.

Details of the above-described cell sorter are described in Patent Literature 7. Further, in this example, a cell sorter available from On-chip Biotechnologies Co., Ltd. was used (Cell sorter model: On-chip-Sort MS6). In this example, the operating conditions of the cell sorter for cell sorting were as follows.

<Analysis by Cell Sorting>

Figure 11:
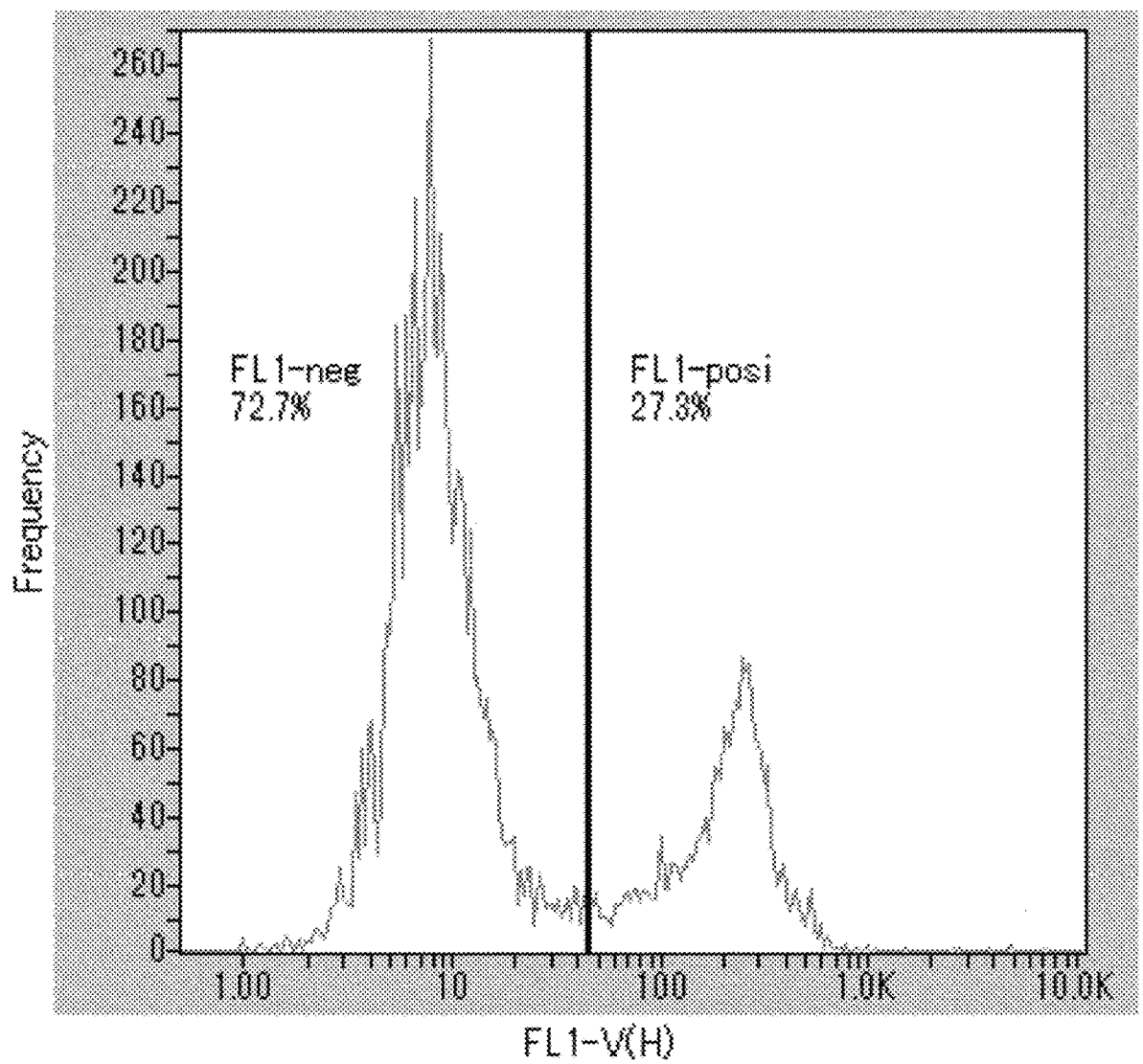
FIG. 11 shows a fluorescence intensity distribution of Hoechst33342.

FIG. 11 shows a fluorescence intensity distribution of Hoechst33342. A vertical axis represents frequencies of appearances of blood cells. A horizontal axis represents intensities of fluorescence signals of Hoechst. There are two peaks. The lowest frequency of appearances was observed between intensities 40 and 50. A border value was defined based on this range, and it was presumed that blood cells for which signal intensities are higher than this border value were nucleated blood cells. Further, it was presumed that blood cells for which signal intensities are lower than this border value were non-nucleated blood cells.

Figure 12:
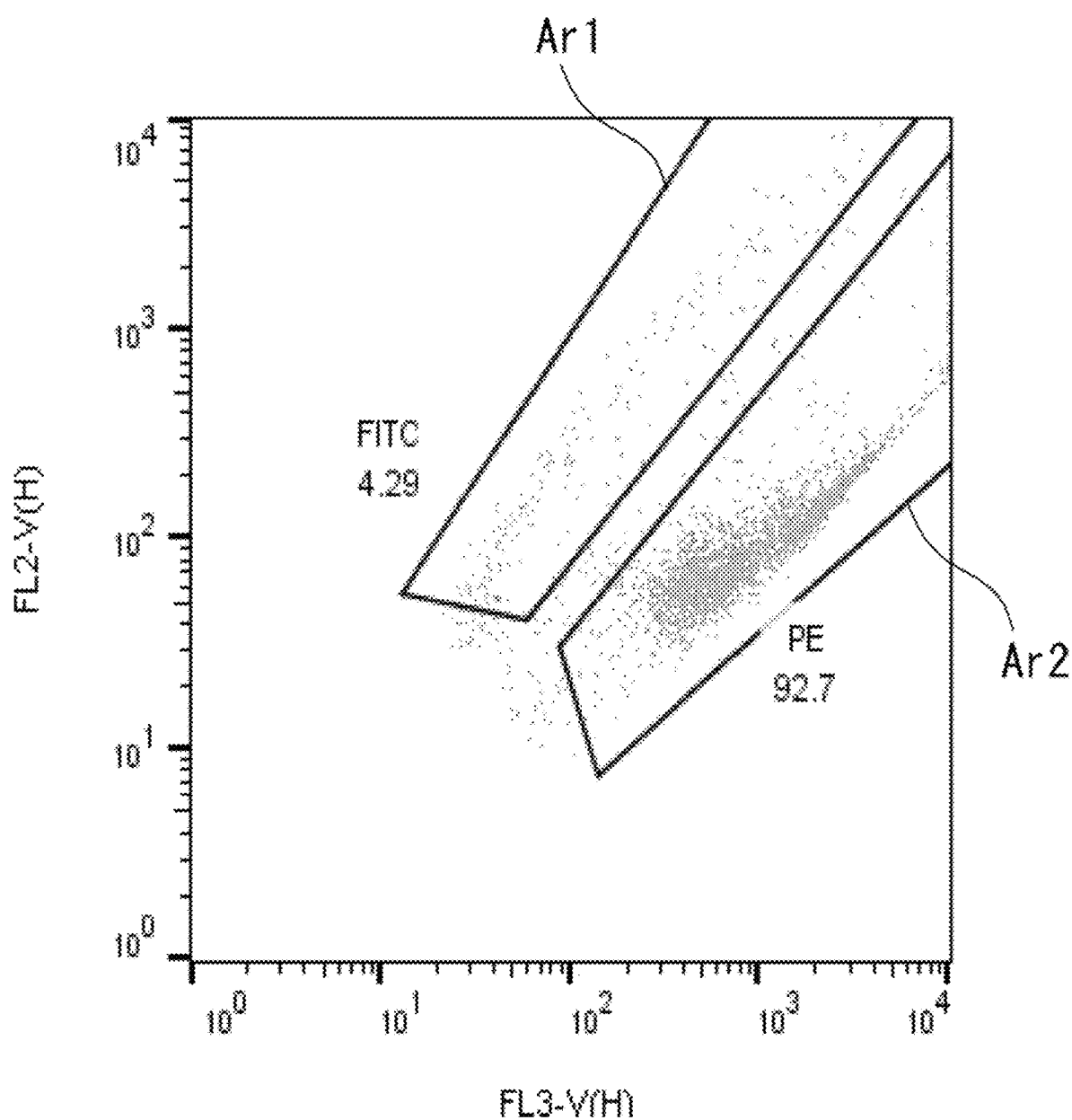
FIG. 12 shows a fluorescence intensity distribution of immunolabeling in maternal blood.
Figure 13:
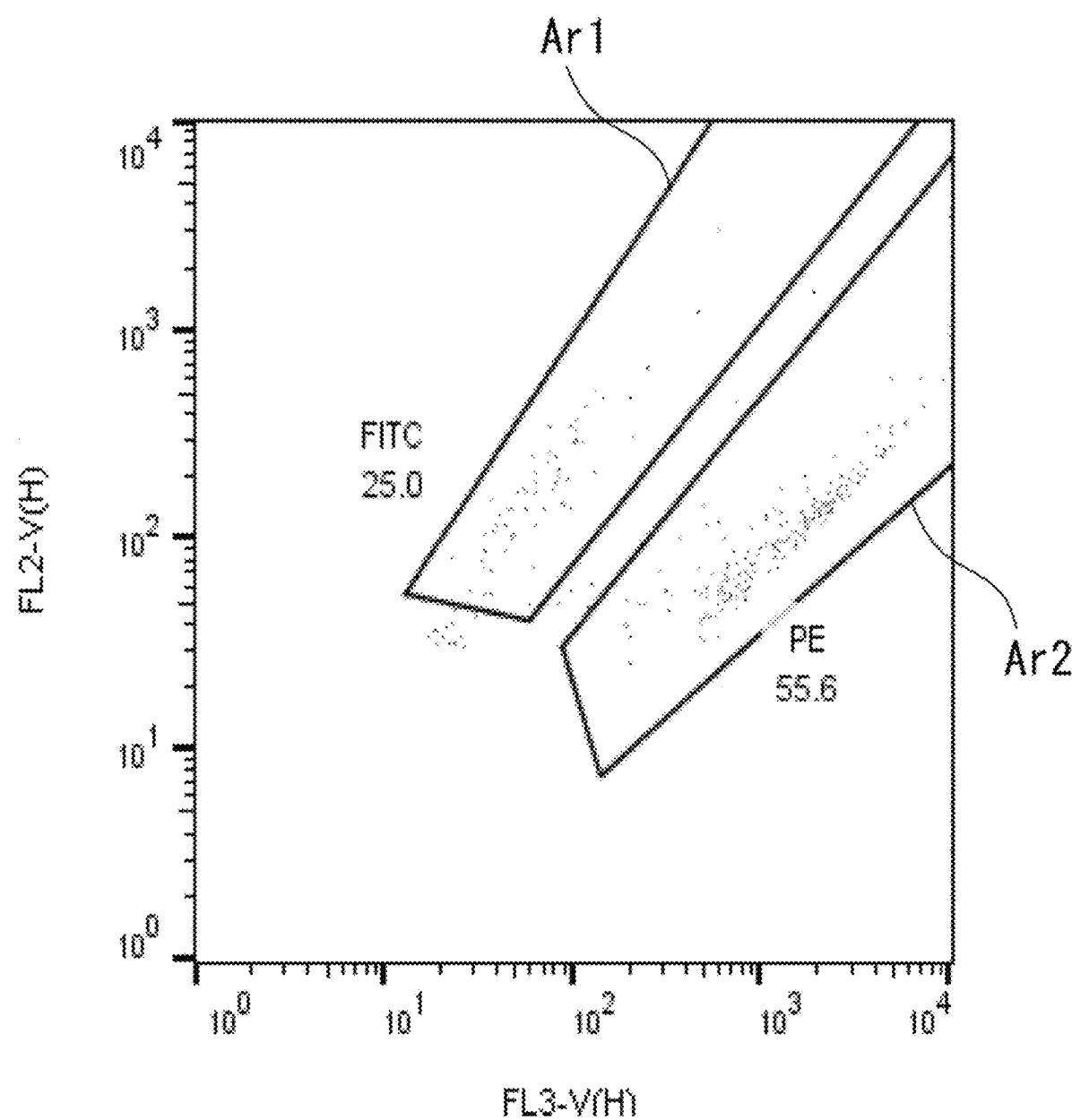
FIG. 13 shows a fluorescence intensity distribution of immunolabeling in ordinary blood.

FIG. 12 shows a fluorescence intensity distribution of immunolabeling in maternal blood. FIG. 13 shows a fluorescence intensity distribution of immunolabeling in ordinary blood. A vertical axis represents intensities of luminescence signals of FITC (fluorescein isothiocyanate) bonded with an anti-CD235a antibody. A horizontal axis represents intensities of luminescence signals of PE (phycoerythrin) bonded with an anti-CD45 antibody.

Ar1 in FIGS. 12 and 13 represents a group of cells in which signals of CD235a-FITC were strong. Ar2 represents a group of WBCs labeled with CD45.

Based on a comparison between the result of the maternal blood and the result of the ordinary blood, it was found that the number of blood cells belonging to the group Ar1 in the maternal blood is larger than that in the ordinary blood.

In FIG. 12, cells in the group Ar1 for which luminescence signal intensities of FITC (fluorescein isothiocyanate) were higher than $1 \times 10^3$ were selected as candidates for NRBCs. This threshold was determined based on the fact that background noises, i.e., luminescence signal intensities of FITC of WBCs in a preliminary experiment were $1 \times 10^3$ or lower. A fraction B containing candidates for NRBCs was obtained by cell sorting based on the above-described examination for conditions.

<Molecular Biological Analysis>

DNA was extracted from the whole fraction B by using Nucleospin Tissue XS. It is also possible to first separate a cell at a single-cell level and then extract DNA. Further, it is also possible to perform whole genome amplification for DNA obtained from a cell separated at the single-cell level. The whole genome amplification can be performed, for example, by using MALBAC available from Yikon Genomics.

Figure 14:
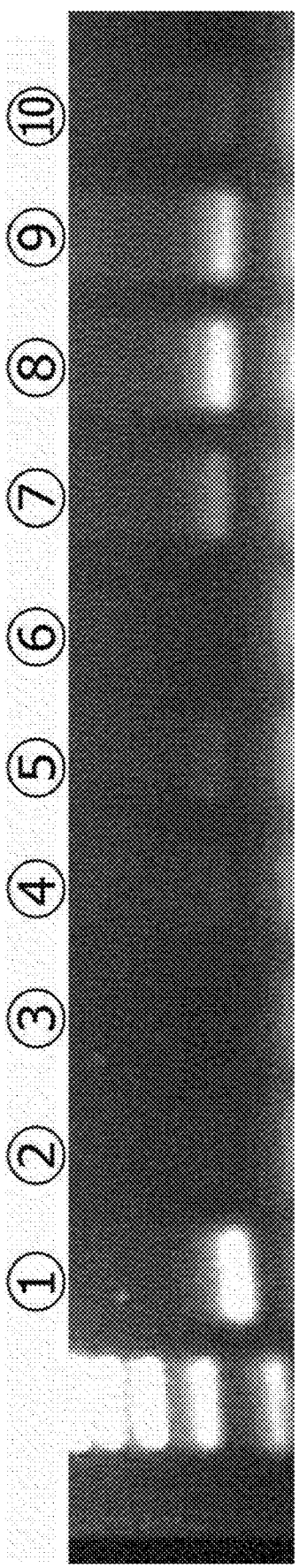
FIG. 14 is an electrophoretic image of DNA of an amplified SRY gene sequence.

In this example, a PCR reaction was performed with extracted DNA as a template by using DNA obtained by the DNA extraction as a template. In the PCR reaction, Ex-Taq polymerase was used. FIG. 14 shows a result of the molecular biological analysis. Lanes 1 to 11 in an electrophoretic image shown in FIG. 14 indicate amplification products having a length of 270 bp by a PCR for an SRY gene sequence. The templates are as follows.

200 bp DNA ladder is shown on the left side of the lane 1.

Lane 1: Standard DNA of Human male, 200 copies.
Lane 2: Standard DNA of Human female, 200 copies.
Lane 3: Standard DNA of Human male, 0 copies.
Lane 4: Standard DNA of Human male, 1 copy.
Lane 5: Standard DNA of Human male, 4 copies.
Lane 6: Standard DNA of Human male, 8 copies.
Lane 7: Standard DNA of Human male, 16 copies.
Lane 8: Standard DNA of Human male, 64 copies.
Lane 9: Standard DNA of Human male, 100 copies.
Lane 10: Sample 1

From the electrophoretic image shown in FIG. 14, it was found that the sample 1 contained DNA having 4 to 16 copies of the SRY gene sequence. Therefore, it was found that the sample 1 contained chromosomal DNA derived from a fetus.

Example 2

In this example, blood collected from a pregnant woman in 33th week of pregnancy was used. The sex of the fetus was male.

<Concentration of Maternal Blood by Blood-Cell Separation Chip>

In Example 2, 0.3 ml of maternal blood was used and its concentration process was performed by using a blood-cell separation chip. As the blood-cell separation chip, for example, one shown in Patent Literature 11 can be used. The blood-cell separation chip fractionates blood cells in a maternal sample based on the sizes of cells.

Figure 15:
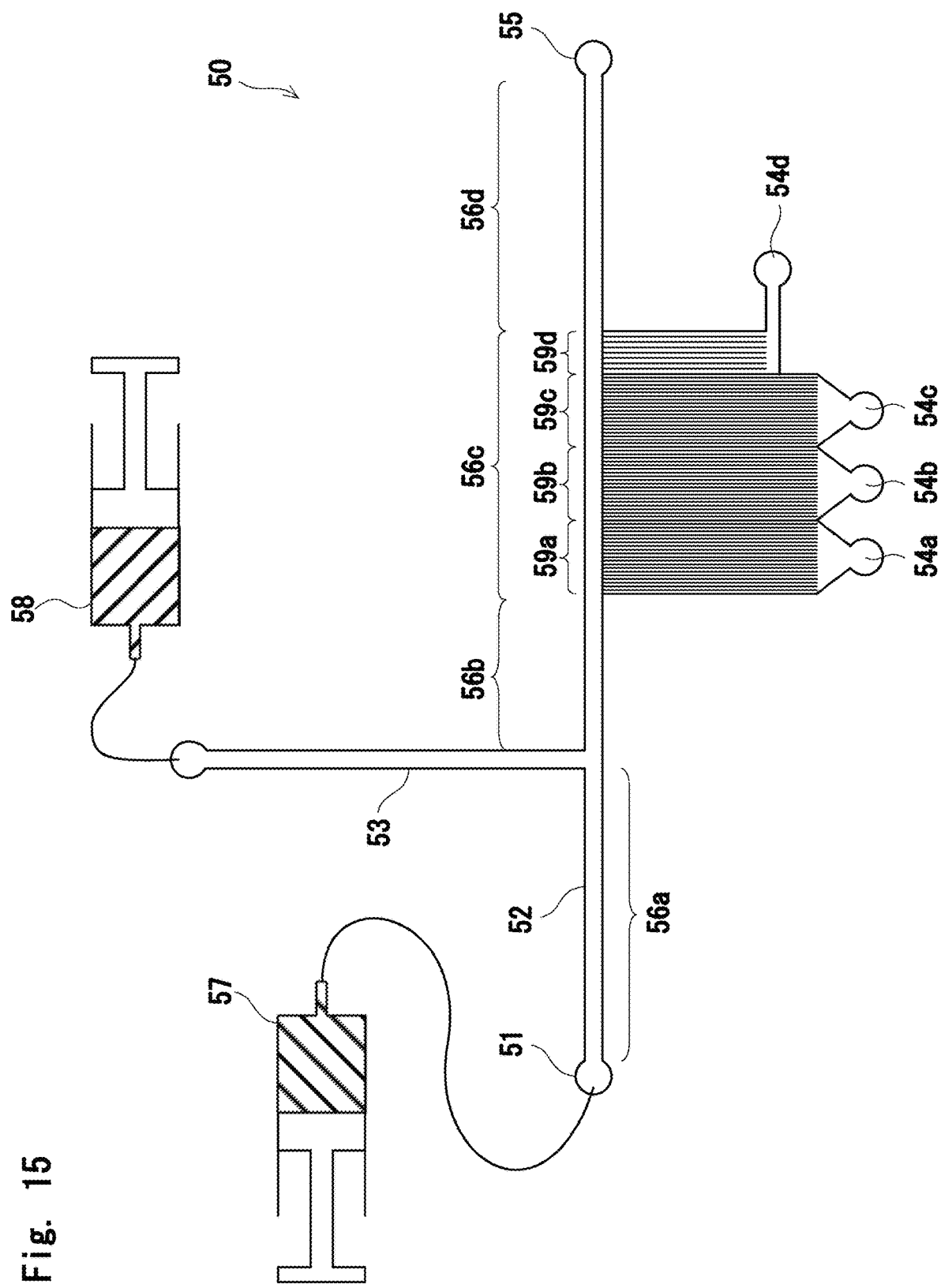
FIG. 15 is a plan view of a blood-cell separation chip.

FIG. 15 shows a plan view of a blood-cell separation chip 50 as an example of the blood-cell separation chip. The blood-cell separation chip 50 includes an inlet 51, a main channel 52, a sub channel 53, and outlets 54a-54d and 55. The main channel 52 includes channels 56a to 56d successively arranged from the inlet 51 toward the outlet 55. The channels 56a to 56d are connected with one after another from the inlet 51 toward the outlet 55.

The inlet 51 shown in FIG. 15 is connected to a syringe 57 containing maternal blood. The maternal blood is sent from the syringe 57 to the inlet 51 at a predetermined flow rate. The maternal blood enters the channel 56a through the inlet 51. Two to three hours had already passed from the collection of maternal blood when the concentration of the blood was started.

The maternal blood is preferably diluted in advance. The dilution ratio can be 2 to 500. In this example, the dilution ratio was 50. The maternal blood is diluted with phosphate buffered saline. The flow rate per unit time of the diluted maternal blood can be 1 to 1,000 µl/min In this example, the flow rate was 25 µl/min. Fractionation using a blood-cell separation chip was performed for ten hours. For example, 15 ml of diluted maternal blood can be processed in one fractionation process.

The blood-cell separation chip 50 shown in FIG. 15 includes a sub channel 53. The sub channel 53 is connected to a syringe 58. The syringe 58 contains PBS. By applying a pressure on the syringe 58, the PBS flows through the sub channel 53 into a channel 56b.

Each of branch channels 59a to 59d shown in FIG. 15 is a channel branching from the main channel 52. In a channel 56c, the branch channels 59a, 59b, 59c and 59d branch from the main channel 52 one by one in this order from the upstream side.

Each of the branch channels 59a to 59d shown in FIG. 15 includes a plurality of narrow channels branching from the main channel 52. These set of the narrow channels are arranged from the upstream of the main channel 52 to the downstream. The branch channels 59a to 59d extend to outlets 54a to 54d, respectively. The narrow channels of each of the branch channels 59a to 59d join together immediately before the outlets 54a to 54d, respectively. The channel 56d extends to the outlet 55.

Figure 16:
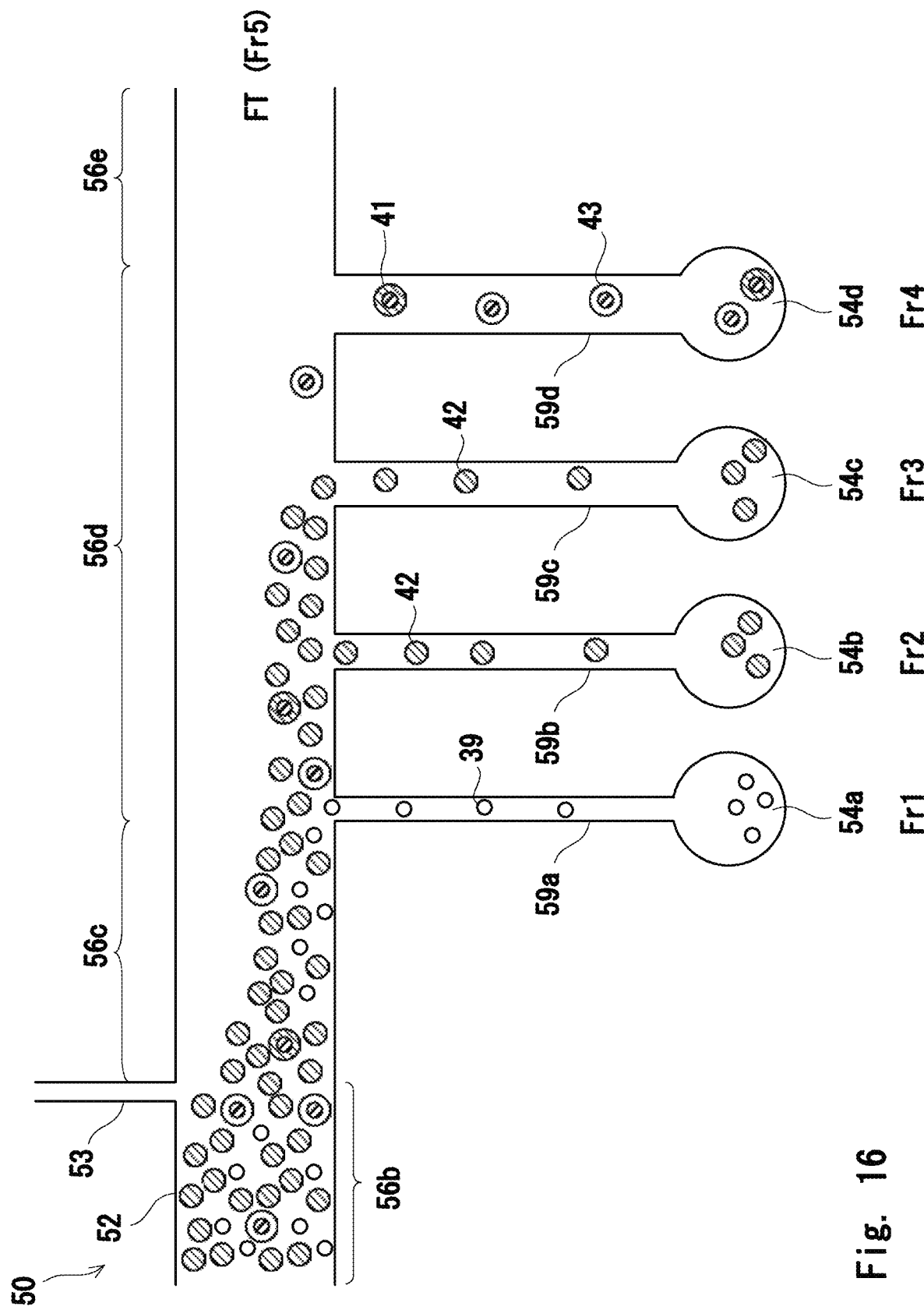
FIG. 16 is a schematic diagram of a blood-cell separation chip.

FIG. 16 schematically shows a process for fractionating blood cells by using the blood-cell separation chip 50. As shown in FIG. 15, each of the branch channels 59a to 59d includes a plurality of narrow channels. In FIG. 16, for each of the branch channels 59a to 59d, only one narrow channel is shown for simplifying the explanation.

Maternal blood flows from the upstream side of the main channel 52 shown in FIG. 16. The maternal blood contains a large number of blood cells. The blood cells reach a channel 56b. Meanwhile, PBS flowing from the sub channel 53 pushes blood cells flowing through the main channel 52 from the side of the main channel 52. In the channels 56b and 56c, blood cells are pushed toward the side of the branch channels 59a to 59d.

In the channel 56a shown in FIG. 16, the branch channels 59a to 59d are arranged on the side of the main channel 52 opposite to the side thereof on which the sub channel 53 is disposed. Inscribed diameters of the narrow channels of the branch channels 59a to 59d increase according to their positions in the arrangement. Note that an inscribed diameter of a narrow channel is a diameter of an inscribed circle on an orthogonal cross section of the narrow channel. In this example, the inscribed diameters of the narrow channels of the branch channels 59a to 59d are 8, 12, 15 and 25 µm, respectively. In this example, a cross-section of a narrow channel has a square shape. The cross section of the narrow channel may have other polygonal shapes or a circular shape.

In the blood-cell separation chip 50 shown in FIGS. 15 and 16, four branch channels are provided. There is no particular limitation on the number of branch channels as long as the number is not less than two. For example, at least two branch channels may be provided. Among the two branch channels, the inscribed diameter of the narrow channel disposed on the upstream side may be 12 to 19 nm. The inscribed diameter of the narrow channel on the upstream side may be any of 13, 14, 15, 16, 17 and 18 nm. The branch channel 59c of the present example corresponds to this narrow channel. The branch channel 59c can be regarded as a channel for removing non-nucleated RBCs.

Meanwhile, the inscribed diameter of the narrow channel disposed on the downstream side may be 20 to 30 nm. The inscribed diameter of the narrow channel disposed on the downstream side may be any of 21, 22, 23, 24, 25, 26, 27, 28, 29 and 29 nm. The branch channel 59d of the present example corresponds to this narrow channel. The branch channel 59d can be regarded as a channel for collecting NRBCs.

The blood cells pushed by the sub channel 53 flow into the branch channels 59a to 59d shown in FIG. 16. The diameter of blood cells flowing into each branch channel is slightly smaller than the inscribed diameter of the narrow channel of that branch channel. In the figure, granules 39 are shown as blood cells slightly smaller than the inscribed diameter of the narrow channel of the branch channel 59a. The granules 39 reach the outlet 54a. In the figure, non-nucleated RBCs 42 are shown as blood cells slightly smaller than the inscribed diameters of the narrow channels of the branch channels 59b and 59c. The non-nucleated RBCs 42 reach the outlets 54b and 54c.

It is considered that the diameter of NRBCs is 11 to 13 nm. In the figure, NRBCs 41 are shown as blood cells slightly smaller than the inscribed diameter of the narrow channel of the branch channel 59d. Further, WBCs 43 are shown. The NRBCs 41 and the WBCs 43 reach the outlet 54d.

The blood cells that have not taken into the branch channels 59a to 59d shown in FIG. 16 pass through the channel 56d together with plasma as flow-through (FT) and reach the outlet 55 shown in FIG. 15. For example, aggregated blood cells and the like are included in the flow-through. A reservoir for receiving fluid is provided in each of the outlets 54a to 54d and the outlet 55.

Fractions Fr1 to Fr4 are sorted out into respective reservoirs connected to the outlet 54a to 54d, respectively, shown in FIG. 16. The flow-through is sorted out as a fraction Fr5 into the reservoir connected to the outlet 55 shown in FIG. 15. Through the above-described processes, blood cells can be fractionized based on their sizes by the blood-cell separation chip 50. Further, since the blood-cell separation chip functions as sieves, the fractions Fr1 to Fr4 do not contain any particles larger than the diameters of the respective narrow channels. Therefore, it is possible to prevent aggregated blood cells from being mixed in the fraction Fr4.

The concentration method using the size of blood cells has advantages over the method using the volumetric mass density. One of the advantages is that while the effect on the volumetric mass densities of blood cells due to the elapse of time after the collection of blood is large, the effect on the size of blood cells due to the elapse of time is small. This means that the method according to this example can be easily carried out even when the place where blood is collected is far from the place where blood cells are fractionated. Another advantage is that, for example, as shown in the above-described operation of the blood-cell separation chip, the fractionation based on the size can be performed by a simple operation.

<Actual Fractionation>

A Table 1 shows a result of fractionation of 15 ml of diluted maternal blood using the above-described blood-cell separation chip. The maternal blood contains 300 µl of maternal whole blood. It is presumed that $1.43 \times 10^9$ blood cells are contained in the maternal whole blood. Measurement was carried out by using a fully-automatic cell counter TC20. The Table 1 shows the numbers of blood cells of fractions that passed through branch channels 1 and 2, and a flow-through 3.

TABLE 1

| | Diameter of Channel (μm) | Number of Blood Cells | Ratio (%) |
|---|---|---|---|
| Fr1 | 8 | $8.46 \times 10^7$ | 18 |
| Fr2 | 12 | $1.48 \times 10^8$ | 32 |
| Fr3 | 15 | $1.97 \times 10^8$ | 45 |
| Fr4 | 25 | $3.29 \times 10^7$ | 7 |
| Fr5 | FT | $7.93 \times 10^5$ | 0 |

The number of blood cells in a fraction Fr4 shown in the Table 1 was $3.29 \times 10^7$. In consideration of the result of the density gradient layered centrifugation, it is considered that this fraction contains blood cells corresponding to NRBCs and WBCs. The fraction Fr4 was used as the above-described fraction A and analyzed by cell sorting.

In the density gradient centrifugation method in the Example 1, it is necessary to collect a fraction(s) floating in the centrifuge tube. In contrast to this, in this example using the blood-cell separation chip, a fraction A can be sorted out by the blood-cell separation chip itself. Therefore, it is possible to simplify the concentration operation for obtaining the fraction A.

<Sorting of Fraction B by Cell Sorting>

A fraction B was sorted out in a manner similar to the Example 1. Firstly, the fraction A was stained with Hoechst33342 and a PE-labeled anti-CD45 antibody. The staining was carried out without performing a fixing process including crosslinking/fixing for cells. Next, staining with an FITC-labeled anti-CD235a antibody was performed. The concentration of the antibody was optimized in a manner similar to the Example 1.

Then, $3.29 \times 10^7$ blood cells of the fraction Fr4 were sorted out by a cell sorter available from On-chip Biotechnologies Co., Ltd. Blood cells that were positive for Hoechst33342 and CD235a and negative for CD45 were sorted out. The selection of those negative for the CD45 may be performed by immunological removal by affinity purification using CD45 antibody beads. Through the above-described processes, a fraction B containing 661 blood cells was obtained.

<Separation at Single-Cell Level>

Figure 17:
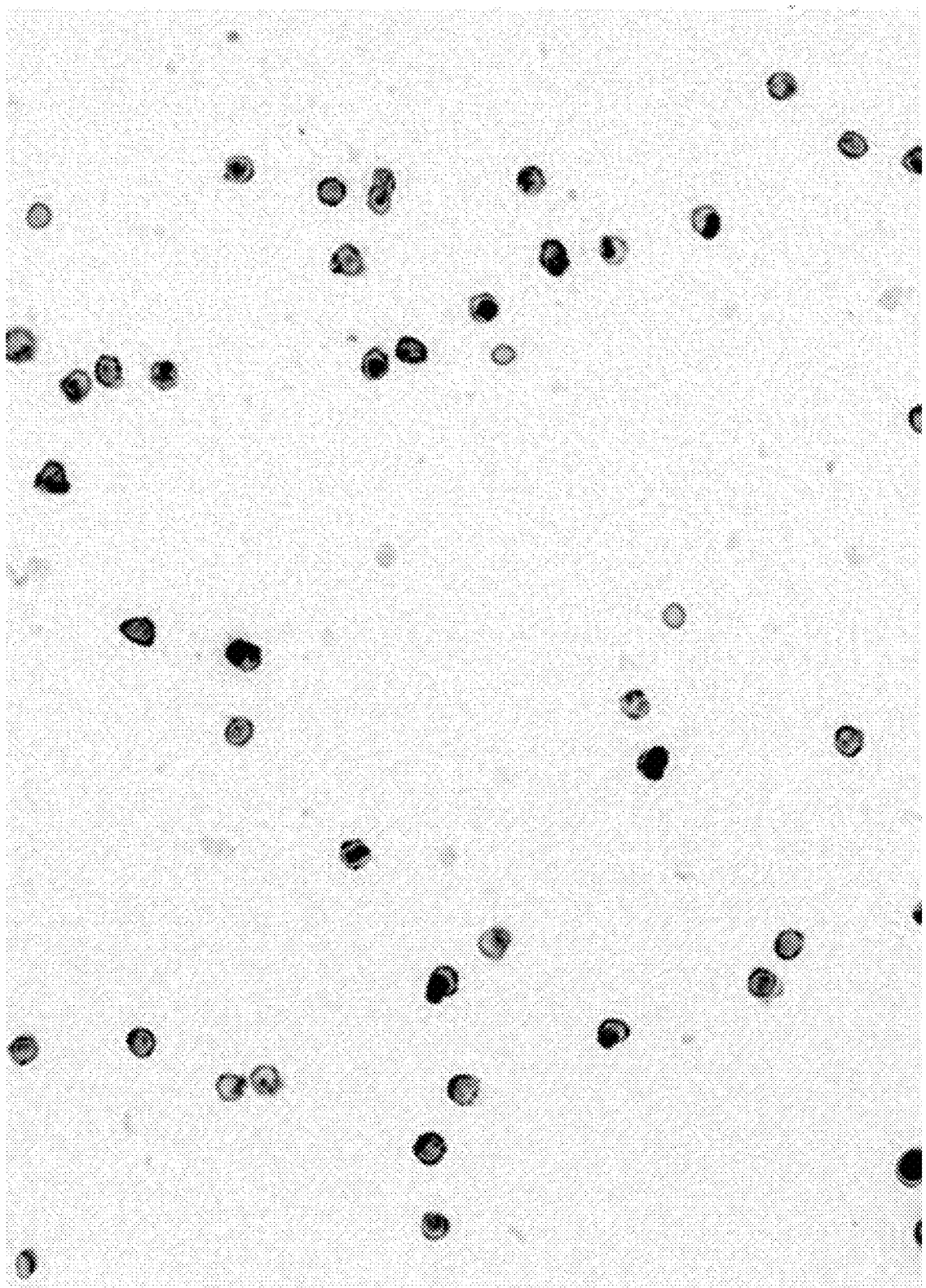
FIG. 17 is a stained image of blood cells.

FIG. 17 shows blood cells that were stained as described above. As shown in the figure, formation of aggregations was prevented. Therefore, it has been shown that blood cells can be separated from each other at a single-cell level. It is considered that aggregations were prevented in this example because the concentration of the antibody with which blood cells were stained was optimized.

<Extraction of Chromosomal DNA>

The above-described fraction B was divided into three fractions each of which contained 200 blood cells. Each of these fractions is expected to contain one or two NRBCs derived from a fetus.

Figure 18:
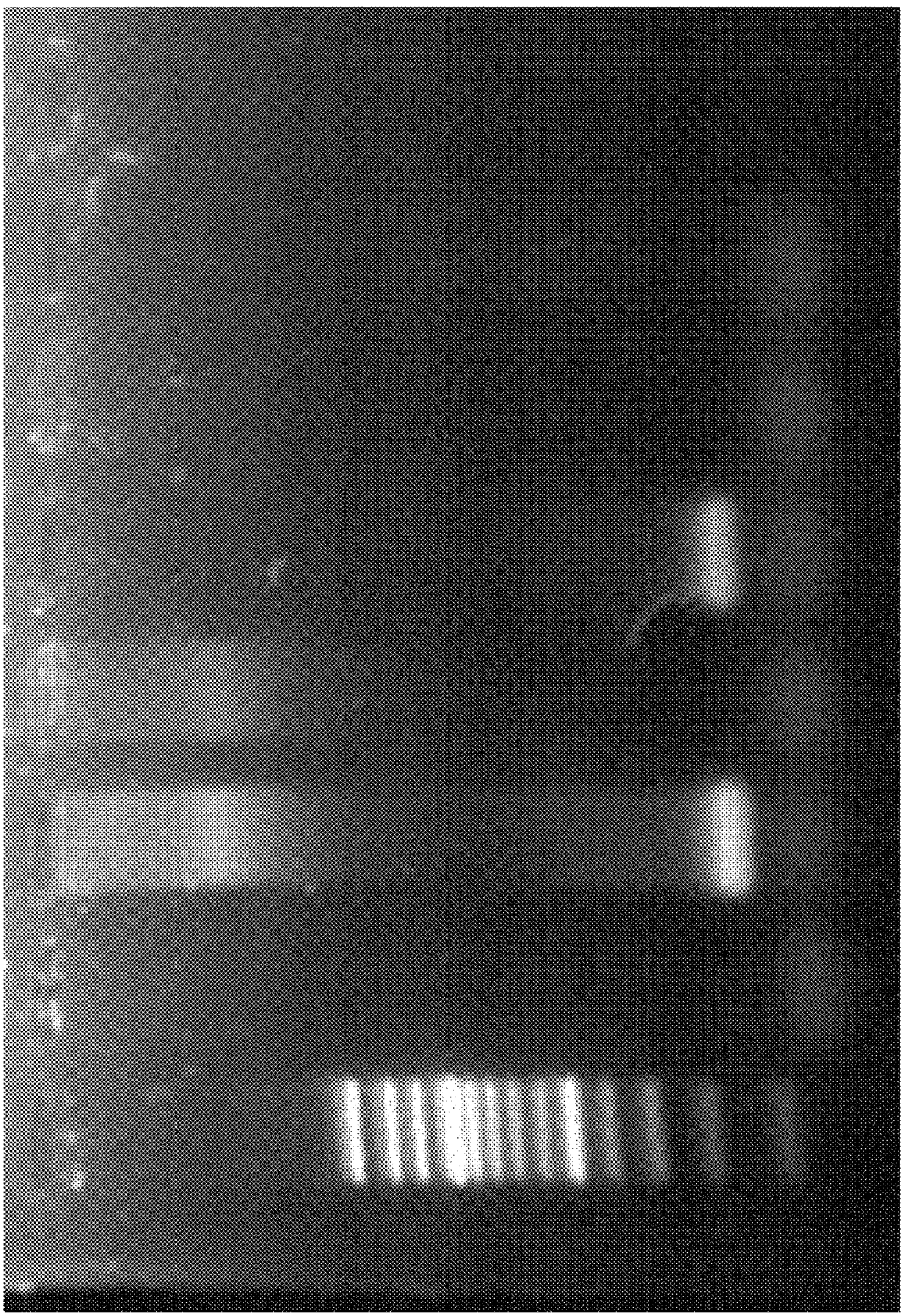
FIG. 18 is an electrophoretic image of DNA of an amplified SRY gene sequence.

Chromosomal DNA was extracted from each fraction. Whole genome amplification was performed for the chromosomal DNA by an MALBAC (Multiple Annealing and Looping Based Amplification Cycles) method. By doing so, a Y-chromosome derived from a fetus was amplified, thus making it possible to easily detect an SRY gene in a later process. Using the amplified chromosomal DNA as a template, PCR amplification specific to an SRY gene sequence was performed. FIG. 18 shows an electrophoretic image of a PCR product of the SRY gene. Templates are as follows.

200 bp DNA ladder is shown on the left side of a lane 1.
Lane 1: distilled water.
Lane 2: Standard DNA of Human male, 20 ng.
Lane 3: Standard DNA of Human female, 20 ng.
Lane 4: Amplification product 1 by MALBAC method, 450 ng.
Lane 5: Amplification product 2 by MALBAC method, 610 ng.
Lane 6: Amplification product 3 by MALBAC method, 700 ng.

An SRY band was observed in lane 4, in which PCR was performed with the amplification product 1 as a template. No SRY band was observed in the PCR in which the other amplification products were used as the template. From the above-described matters, it has been found that it is possible to fractionize and thereby divide the fraction B into a fraction containing blood cells derived from a fetus and a fraction containing no blood cell derived from a fetus. Further, it has been suggested that it is possible to identify the presence or absence of an SRY gene in a blood cell separated at a single-cell level by performing limited dilution at a single-cell level.

Based on the above-described novel finding, it is considered that those skilled in the art can easily understand that it is possible to obtain chromosomal DNA that is distinguishable at a single-cell level and is derived from a fetus. That is, while three fractions each of which contains 200 blood cells were obtained in this example, it is possible, in other methods, to separate blood cells at a single-cell level by dividing the fraction B into fractions each of which contains 600 blood cells by the limited dilution method. The above-described fractionation may be performed indiscriminately, or may be performed while confirming that each of obtained small fractions contains one cell. Further, it is possible to perform a certain DNA extraction process and an amplification process for these small fractions containing blood cells at a single-cell level.

In general, chromosomal DNA corresponding to one cell has only a single copy of gene or allele, which is derived from a gamete of each parent. However, the whole genome amplification method including an MALBAC method can amplify one copy of such a DNA sequence by using chromosomal DNA corresponding to one cell as a template. The amplified DNA can be suitably used for obtaining molecular biological data necessary for prenatal testing or a prenatal diagnosis.

Reference Example: Picking Method

Patent Literature 4 discloses the so-called picking method. In the picking method, blood cells stained by May-Giemsa stain are observed on a glass slide and NRBCs are isolated based on their morphology. In this method, NRBCs are isolated at a single-cell level. Therefore, a fraction containing no white blood cell can be obtained. Therefore, purity of chromosomal DNA of fetal cell origin obtained from such a fraction is extremely high. Regarding the purity mentioned here, attention is paid to the presence or absence of mixing of chromosomal DNA of a cell of maternal origin.

However, in Patent Literature 4, it is mentioned that any of five cells that were identified as most likely to be NRBCs by a morphological observation, i.e., any of five cells ranked at the top was not an NRBC derived from a fetus (Paragraph 0078). In Patent Literature 4, there was no choice, but five cells ranked in the next highest positions were molecular-biologically analyzed and one cell derived from a fetus was obtained from them (paragraph 0079).

When a prenatal diagnosis is performed, needless to say, the amount of a maternal blood sample that can be collected from a subject is limited. Further, it is obstetrically obvious that there is only a limited period during which a prenatal diagnosis can be performed for each pregnant woman, i.e., for each subject of the diagnosis. Further, the number of NRBCs derived from a fetus in blood is extremely small. Therefore, a method capable of testing the whole amount of a sample in a limited period is desired. In other words, there is no need for a method that is performed on the precondition that when an acquisition of a cell derived from a fetus is found to have failed, the acquisition process is repeated again.

The method based on a morphological observation is reliable because an NRBC can be reliably collected. However, as the cost for the high reliability, a reasonable expectation that an NRBC derived from a fetus may be obtained within a certain time period is compromised.

Further, since NRBCs of maternal origin are also contained in maternal blood, it is very difficult to sort out NRBCs derived from a fetus by a morphological observation. Sorting of candidates for NRBCs derived from a fetus based on morphological information needs to be substantiated by a molecular biological analysis.

Further, in the course of the research of the present invention, the inventors have found that, in the picking method, an operator needs to have sufficient skill to transport an identified NRBC from a preparation to a container. Meanwhile, the inventor has also found that in a state in which blood cells are sufficiently concentrated as in the case of the above-described embodiment and the example, it is possible to obtain chromosomal DNA derived from an NRBC originated from a fetus even by an indiscriminate molecular biological analysis at a single-cell level.

Based on the above-described findings, priority is not given to the isolation of NRBCs in the above-described embodiment and the example. Instead, priority is given to the collection of chromosomal DNA derived from a fetus that can be eventually distinguished at a single-cell level. It has been found that in order to achieve the above-described priority target, it is more efficient to first perform indiscriminate fractionation by a limited dilution method or the like and then perform an indiscriminate molecular biological analysis.

To perform the indiscriminate molecular biological analysis, it is necessary to prepare a fraction in which NRBCs are concentrated at a higher level than the level in fractions used in the method that relies on morphological information. In other words, it is necessary to sufficiently remove other blood cells from the fraction. Otherwise, the number of blood cells that should be molecular-biologically processed becomes enormous, thus making the fraction unsuitable for the molecular biological analysis at a single-cell level. Accordingly, the concentration of NRBCs at a high level is achieved by combining the concentration based on the volumetric mass density or the size with the concentration by cell sorting.

Second Embodiment

Similarly to <<First Embodiment>>, chromosomal DNA derived from an NRBC originated from a fetus isolated at a single-cell level is obtained in the below-described second embodiment and its example. Differences from <<First Embodiment>> are mainly described hereinafter. Technical matters that are omitted in the following description but are necessary for the second embodiment are the same as those described in <<First Embodiment>>.

[Collecting Blood and NRBC]
Details of the collection of blood and the target NRBC are the same as those described in <<First Embodiment>>.

[a. Labeling for Fraction A]
<a-1. Acquisition of Fraction A by Concentration>
An acquisition of a fraction A by a concentration is performed as described in <<First Embodiment>>.

<a-2. Labeling of Fraction A>
In a step S22 shown in FIG. 1, WBCs and cell nuclei in a fraction A are specifically labeled. The labeling (label or labeling) may be magnetic labeling or fluorescent labeling, though the fluorescent labeling is preferred. The labeling may be direct labeling or indirect labeling. The indirect labeling may be labeling made by a tag and a secondary antibody, or may be labeling made by a biotin-avidin bonding.

The labeling specific to WBCs may be labeling specific to surfaces of WBCs. The labeling specific to WBCs may be immunolabeling. The immunolabeling may be labeling made by an antibody. A target antigen of the immunolabeling may be a carbohydrate antigen. The labeling may be labeling made by an antibody for an antigen specific to WBCs such as CD45.

Cell nuclei contained in NRBCs are specifically labeled by labeling specific to nucleic acids. The labeling specific to nucleic acids may be dye labeling. The nucleic acids to be labeled are preferably DNA. The dye may be a fluorescent dye. Nuclei may be fluorescent-labeled by a fluorescent dye. The fluorescent dye may be Hoechst33342. The labeling specific to cell nuclei may be immunolabeling.

In the step S22 shown in FIG. 1, the labeling specific to WBCs and the labeling specific to cell nuclei may be performed at the same time. Alternatively, one of the labeling processes may be performed before the other labeling. Further, one of the labeling processes may be performed before the other labeling and the sorting in the step S23 may also be performed before the other labeling. After that, the other labeling and the sorting may be performed.

Note that histological crosslinking/fixing may be performed for blood cells in the fractions A before one or all of the above-described labeling processes may be performed. Further, the below-described fractionation by cell sorting may be performed in this state. It is possible to prevent blood cells from aggregating by crosslinking/fixing blood cells. Therefore, the fractionation by cell sorting can be accurately performed. Extracted DNA may be de-crosslinked before a molecular biological analysis is performed in the later-described step d.

The below-described fractionation, i.e., fractionation by cell sorting may be performed without performing histological crosslinking/fixing for blood cells in the fraction A. In this way, it is possible to minimize the effect caused by the crosslinking/fixing in a molecular biological analysis performed in the later-described step d.

For example, labeling specific to cell nuclei and labeling specific to WBCs may be performed at the same time without performing crosslinking/fixing of blood cells. Further, blood cells may be crosslinked/fixed after these labeling processes are performed. Further, immunolabeling specific to RBCs may be performed for crosslinked/fixed blood cells.

[b. Acquisition of Fraction B by Cell Sorting]
<b-1. Basic Cell Selection>
In a step S23, a fraction B is obtained by sorting out labeled blood cells in the fraction A by cell sorting. The principle of the cell sorting and the type of the cell sorter are the same as those described in <<First Embodiment>>.

In the step S23 shown in FIG. 1, blood cells are preferably sorted so that blood cells that have been labeled with the WBCs specific label are removed. Since NRBCs are RBCs, the NRBCs can be distinguished from WBCs by the labeling specific to WBCs.

In the step S23 shown in FIG. 1, the blood cells are preferably sorted out so that blood cells that have been labeled with the label specific to nucleated blood cells are obtained. Since NRBCs have cell nuclei, the NRBCs can be distinguished from non-nucleated RBCs by the labeling specific to cell nuclei.

In the step S23 shown in FIG. 1, a fraction B having increased purity of NRBCs is obtained by combining the above-described labeling processes. The obtained fraction B includes NRBCs of maternal origin and NRBCs derived from a fetus. The removal of WBCs by the labeling specific to WBCs and the collection of nucleated blood cells by the labeling specific to cell nucleus may be performed at the same time. Alternatively, one of the removal and the collection may be performed before the other process. For example, a fraction B may be obtained by first removing WBCs by magnetic labeling specific to WBCs and then performing sorting by using fluorescent labeling specific to cell nuclei.

In the step S22 shown in FIG. 1, RBCs in the fraction A may be specifically labeled in an additional manner. The labeling specific to RBCs may be immunolabeling. This labeling may be labeling for an antigen specific to RBCs such as CD71 and CD235a. The antigen may be a carbohydrate antigen. In the step S23, blood cells are preferably sorted so that blood cells that have been labeled with the label specific to RBCs are collected.

<b-2. Additional Cell Selection>

Additional Cell Selection may be performed. A method for the Additional Cell Selection may be similar to a method described in <<First Embodiment>>.

[c. Separation of Blood Cell and Nucleic Acid Extraction]

In a step c, each of the blood cells in the fraction B is separated at a single-cell level. Further, a process for extracting a nucleic acid is independently performed for each of the separated blood cells. In this way, fractions C each of which contains a nucleic acid distinguishable at a single-cell level are obtained. The nucleic acid may be DNA or RNA. Further, in addition to the acquisition of a fraction of DNA, a fraction of RNA may also be extracted from a single cell from which the fraction of the DNA has been obtained. The DNA may be chromosomal DNA. In this example, chromosomal DNA means a genomic DNA. The RNA may be an mRNA or a non-coding RNA. The mRNA and the non-coding RNA may be a full length or a partial sequence.

"c-1. Separation of Blood Cell at Single Cell Level" is performed as described in <<First Embodiment>>. A limited dilution method is preferably used for the separation of blood cells at a single-cell level. As a type of the limited dilution method, blood cells may be separated at a single-cell level by using an apparatus that discharges droplets containing granular substances.

As an example of the limited dilution using a discharge apparatus, Patent Literature 13 discloses a method using a discharge apparatus. This discharge apparatus discharges a droplet having a volume that is determined so that the droplet contains one blood cell toward a target container by using an actuator such as a piezo device. Note that the discharge apparatus separates blood cells at a single-cell level by first selecting one of a plurality of containers for each blood cell and then discharging a droplet toward the selected container.

After the separation of blood cells at a single-cell level, a fraction C is obtained. When the nucleic acid to be obtained from a fetal cell is chromosomal DNA, "c-2. Acquisition of Fraction C by DNA Extraction" is performed as described in <<First Embodiment>>. When RNA is included in the nucleic acid to be obtained from a fetal cell, "c-3. Acquisition of Fraction C by RNA Extraction" is performed as follows. As described above, an extraction of RNA from a blood cell and an extraction of chromosomal DNA therefrom may be performed at the same time.

<c-3. Acquisition of Fraction C by RNA Extraction>

Figure 19:
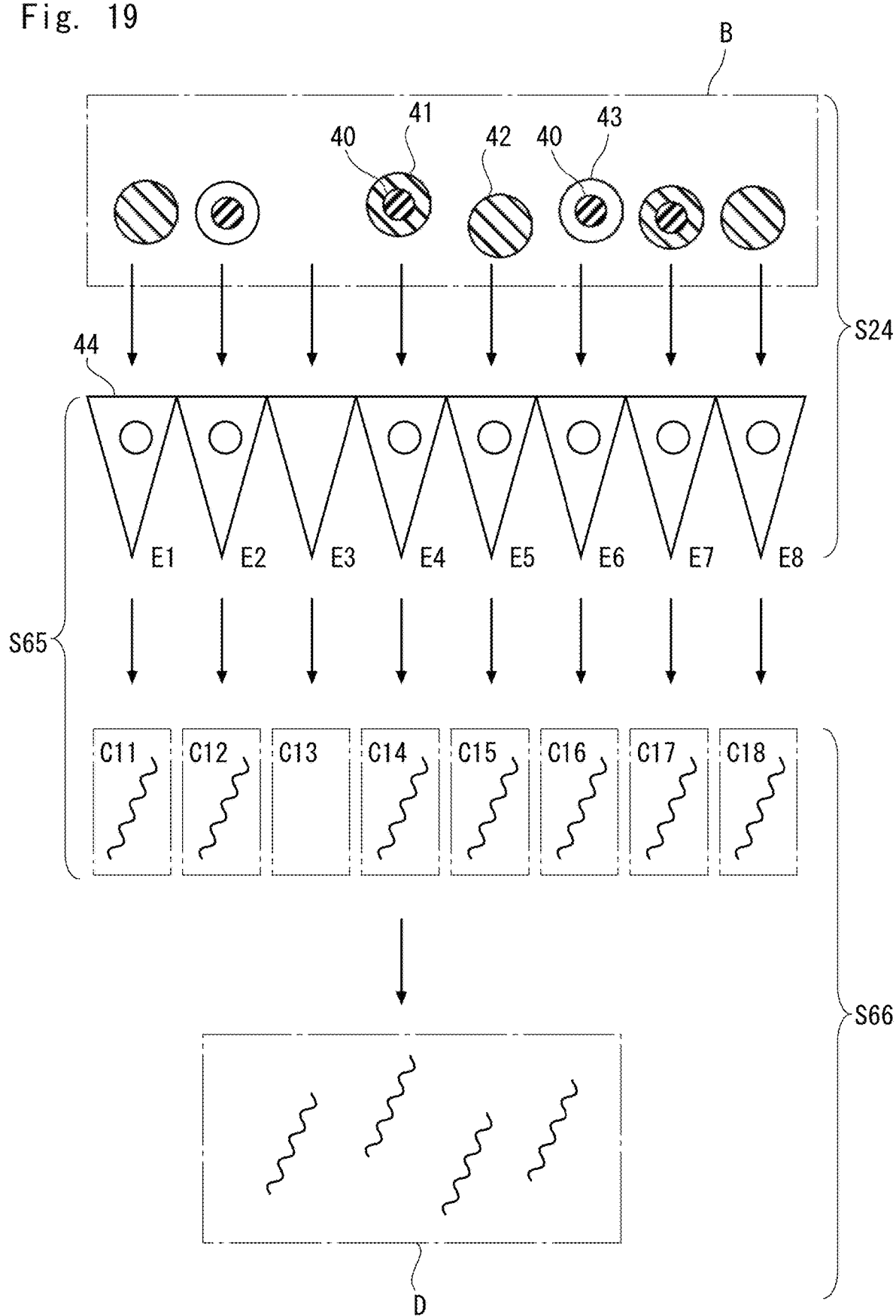
FIG. 19 is a conceptual diagram showing a separation at a single-cell level and an RNA extraction.

FIG. 19 schematically shows separation at a single-cell level and an RNA extraction. After performing the step S24 shown in FIG. 1, RNA is extracted without performing the step S25 as shown in FIG. 19. In a step S65, fractions C are obtained by independently performing a process for extracting RNA for each separated blood cell. By performing the steps S24 and S65, each of the fractions C contains RNA distinguishable at a single-cell level. In this embodiment, the fraction containing RNA capable for tracing back it to a blood cell before RNA extraction at a single-cell level includes a fraction containing RNA extracted from a single blood cell.

As shown in FIG. 2, it is preferable to indiscriminately perform a process for extracting RNA for the fractions E1 to E8 containing blood cells sorted out into the individual containers 44. The extraction process is indiscriminately performed irrespective of whether or not each of blood cells contained in the fraction B has a characteristic of an NRBC. Further, the extraction process is indiscriminately performed irrespective of whether or not a blood cell contained in each of the fractions E has a characteristic of an NRBC. That is, the extraction process is performed irrespective of whether or not each blood cell is an NRBC. The term "indiscriminately" is not intended to eliminate concentrations of NRBCs based on their volumetric mass densities and their sizes, and based on their labeling in the processes up to the acquisition of the fraction B.

As a result of the extraction process, fractions C11, C12 and C14-C18 are obtained as the fractions C. That is, the extraction of RNA from NRBCs 41 does not eliminate at all extractions of RNA from non-nucleated RBCs 42 and WBCs 43. Further, there may be a fraction that is obtained by performing a chemical process for extracting RNA for a fraction containing no blood cells as in the case of the fraction C13.

The RNA extraction process is independently performed at a single-cell level. Therefore, for example, RNA derived from NRBCs 41 is contained in the fractions C14 and C17. Further, RNA of other cells is not mixed in the fractions C14 and C17. As described above, RNA having purity equivalent to that of RNA obtained from NRBCs that are isolated in advance are contained in the fractions C14 and C17. Note that regarding the purity mentioned here, attention is paid to the presence or absence of mixing of RNA of WBCs and RBCs of maternal origin.

As shown in FIG. 2, the extractions of RNA are indiscriminately performed for individual blood cells. That is, the extraction process is performed irrespective of whether or not each blood cell is an NRBC. As a result, RNA of non-nucleated RBCs is contained in the fractions C11, C15 and C18 derived from non-nucleated RBCs 42. RNA of WBCs is contained in the fractions C12 and C16 derived from WBCs 43. Since there was no blood cell in the fraction E3, no RNA is contained in the fraction C13.

The method according to this embodiment allows for the above-described inefficient operations. By indiscriminately separating cells and extracting RNA as described above, RNA of NRBCs can be obtained without relying on the isolation operation including identification of NRBCs. Therefore, the overall efficiency of the series of processes is improved.

In the step c in this embodiment, the following three points should be noted. As the first point, for a person who carries out this embodiment, it is acceptable that the fact that RNA derived from NRBCs are contained in the fractions C14 and C17 among the eight fractions C shown in FIG. 2 is still unknown in the step c. This is because it is not essential to isolate NRBCs based on morphological information in the method according to this embodiment. More specifically, this is because the fractions C are indiscriminately obtained as described above.

As the second point, it is presumed that RNA derived from an NRBC was obtained in one of the fractions C shown in FIG. 2 in an after-the-fact manner by performing a molecular biological analysis in the later-described step d. In general, fetal cells mixed in maternal blood are fetal NRBCs. Therefore, the above-described presumption is made when it is found out that the RNA is derived from a fetus.

As the third point, for a person who carries out this embodiment, it is acceptable that whether RNA contained in the fractions C14 and C17 shown in FIG. 2 are derived from NRBCs of the mother or derived from fetal NRBCs is still unknown in the step c. This is because it is not essential to use means for distinguishing NRBCs of the mother from fetal NRBCs in the aforementioned step. The fact that the RNA is derived from a fetus is found out in an after-the-fact manner by performing a molecular biological analysis in the later-described step d.

An apparatus 74 shown in FIG. 4 may be used in place of the containers 44 shown in FIG. 2. The apparatus 74 includes a channel 75, trapping structures 76, and reaction structures 77. A plurality of trapping structures 76 are successively arranged along the channel 75. The reaction structures 77 are provided for the respective trapping structures 76.

In the apparatus 74 shown in FIG. 4, cells 78 are distributed into each trapping structure 76 and hence the cells 78 are separated from each other at a single-cell level. However, cells 78 trapped by the trapping structures 76 are not sorted out into specific containers. After all the cells 78 or a desired number of cells 78 are trapped in the trapping structures 76, the trapped cells 78 are dissolved and the cells are processed by washing out the dissolved substance toward the reaction structures 77. In the reaction structures 77, extractions of RNA and the below-described reaction for cDNA amplification may be performed as the processes for cells.

As the apparatus 74 shown in FIG. 4, a micro-fluid device disclosed in Patent Literature 9 may be used. Further, as the micro-fluid device, C1 Single-Cell Auto Prep Array IFC available from Fluidigm Corporation may be used.

The extraction of RNA and the extraction of chromosomal DNA may be performed at the same time as described later in <d-3. Supplementary Note for Simultaneous Extraction and Analysis of Chromosomal DNA and RNA>.

[d. Selection of Fraction D by Analysis on Nucleic Acid]

When the nucleic acid obtained from a fetal cell is chromosomal DNA, "d-1. Selection of Fraction D by DNA Analysis" is performed as described in <<First Embodiment>>. As shown in a step S28 shown in FIG. 5, for example, whole genome amplification may be performed for the chromosomal DNA in the fraction C. Instead of extracting the whole genome, a partial area in the genome may be amplified. After that, a molecular biological analysis is performed in a step S29 and a fraction D is selected in a step S30 as described in <<First Embodiment>>.

When the nucleic acid obtained from a fetal cell is RNA, "d-2. Selection of Fraction D by RNA Analysis" is performed as follows.

<d-2. Selection of Fraction D by RNA Analysis>

In a step S66 shown in FIG. 19, a molecular biological analysis is performed for each of the fractions C. By doing so, a fraction D containing RNA derived from a fetus or a cDNA derived from the RNA derived from a fetus is selected from the group of fractions C.

Figure 20:
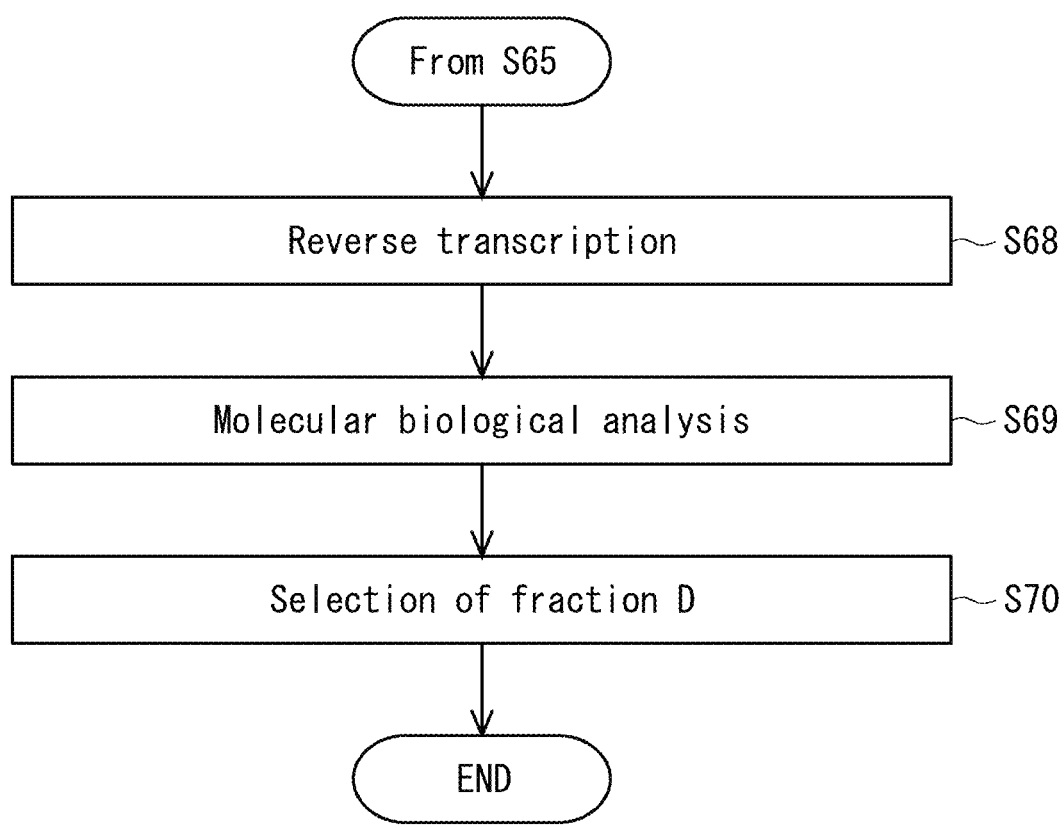
FIG. 20 is a flowchart for a selection of a fraction D.

FIG. 20 shows a preferred example of the step S66 shown in FIG. 19. In a step S68 shown in FIG. 20, reverse transcription is performed by using the RNA in the fraction C as a template. By the reverse transcription, the fraction C becomes a fraction containing cDNA having a sequence complementary to that of RNA in abundance. Hereinafter, the fraction that contains cDNA as a result of the reverse transcription is also referred to as the fraction C. RNA in the fraction C may be digested after the reverse transcription.

In a step S29 shown in FIG. 5, a molecular biological analysis is performed. In this way, it is distinguished whether RNA in each fraction C is of maternal origin or derived from a fetus. In the distinction, the following points may be noted.

In this embodiment, RNA of maternal origin is distinguished from RNA transcribed from genomes of mother origin. The RNA of maternal origin is exclusively derived from somatic cells of the mother's body.

In this embodiment, the RNA transcribed from a genome of mother origin means a transcription product derived from a chromosome that the fetus inherited from the mother. RNA transcribed from a genome of mother origin means RNA derived from a fetus, unless otherwise specified. Such RNA may be in a state in which the RNA is mixed with RNA derived from a chromosome that the fetus has inherited from the father.

When the mother's body is the same as the mother, a sequence of RNA transcribed from a genome of mother origin is the same as a sequence of RNA of maternal origin. Note that the method according to this embodiment can be applied even when the fetus is derived from an egg derived from a woman other than the mother, instead of being derived from an egg of the mother's body.

As the molecular biological analysis in the step S69 shown in FIG. 20, a method based on an embryonic epsilon globin gene related to a beta globin gene (Non-patent Literature 2) is preferred. Since the embryonic epsilon globin gene is expressed specifically to an embryo, fetal cells and maternal cells (WBCs and other nucleated blood cells) can be distinguished from each other based on the expression level of the transcription product of the epsilon globin gene.

When it is already determined that the fetus is male, an analysis based on a sequence specific to a Y chromosome may be performed. RNA derived from a male fetus contains a sequence derived from a Y-chromosome as a sequence that is not derived from the genome of a mother. Therefore, it is possible to identify that the RNA is derived from a fetus.

In a step S70 shown in FIG. 20, it is checked which of the fractions C is derived from the fetus based on the result of the above-described molecular biological analysis. In this way, it is possible to select a fraction D from the fractions C. Note that since the reverse transcription was performed, the fractions C contain cDNA. The obtained fraction D contains the cDNA.

In the step S70 shown in FIG. 20, it is not essential to confirm that the fraction D is derived from an NRBC without doubt. In the step S70, the morphological information of the blood cell has already been lost. Since the purity of NRBCs is increased in the step S23, it is stochastically presumed that a fraction D derived from an NRBC is obtained.

Through the series of processes shown in FIGS. 1, 19 and 20, it is possible to obtain a fraction D containing a cDNA that is synthesized by using RNA derived from an NRBC originated from a fetus isolated at a single-cell level as a template.

When the reverse transcription is performed, it is necessary to unlink crosslinking that was used for the fixing in the step b. That is, the RNA is de-crosslinked. By doing so, it is possible to efficiently proceed with the reverse transcription and the DNA analysis. Further, the crosslinking may be omitted, so that the RNA is prevented from being damaged in the de-crosslinking reaction.

<d-3. Supplementary Note for Simultaneous Extraction and Analysis of Chromosomal DNA and RNA>

Figure 21:
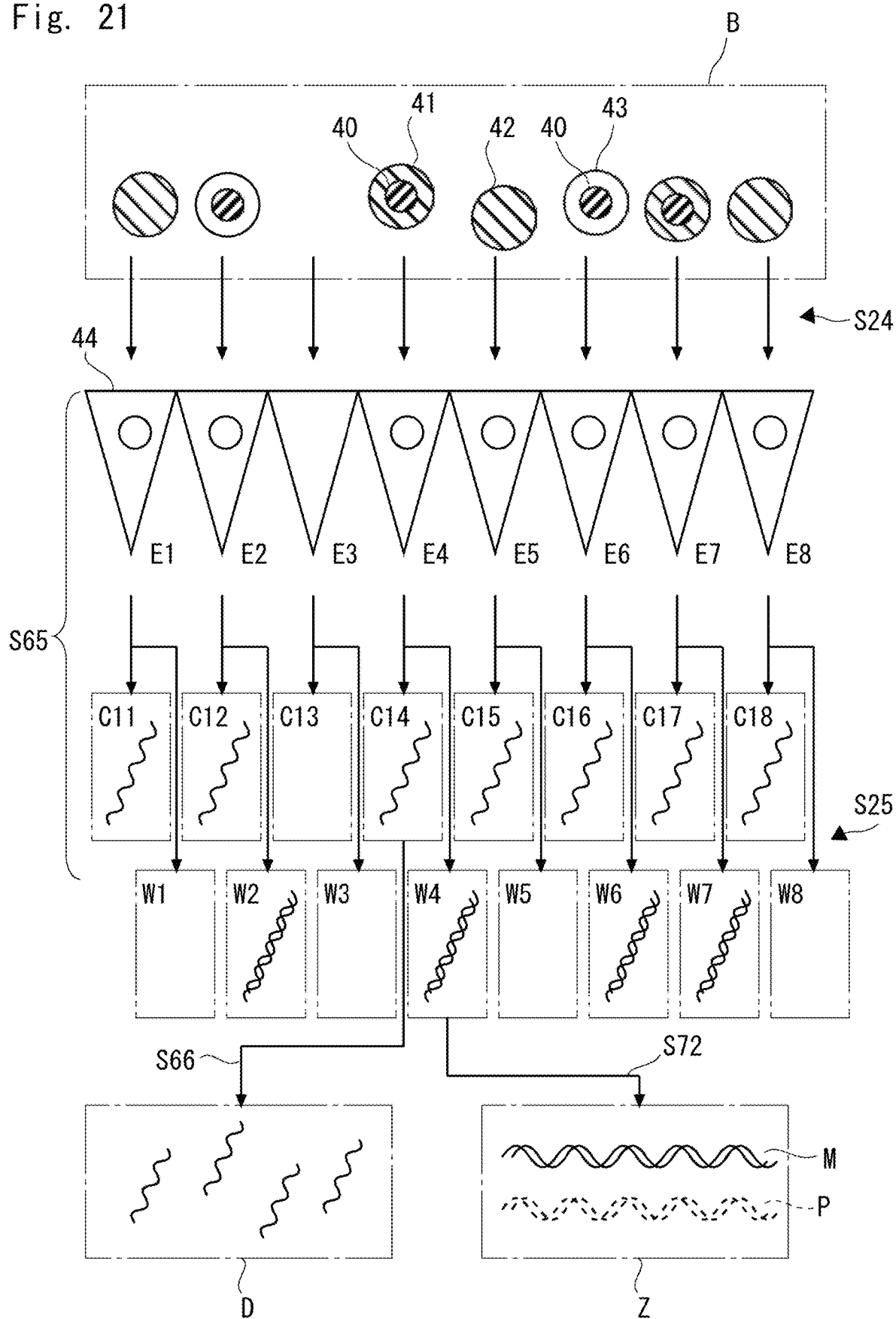
FIG. 21 is a conceptual diagram showing simultaneous extraction of chromosomal DNA and RNA.

FIG. 21 shows simultaneous extractions of chromosomal DNA and RNA. It is preferable to simultaneously acquire fractions W by performing the extraction of RNA shown in the step S65 and the extraction of chromosomal DNA shown in the step S25. In this case, a fraction D is selected by an RNA analysis shown in a step S66, instead of selecting the fraction D by the chromosomal-DNA analysis. In this way, chromosomal DNA derived from a fetal cell separated at a single-cell level can be obtained without performing the chromosomal-DNA analysis.

Based on the result of the selection of the fraction D containing the RNA shown in FIG. 21, a fraction W4 is selected as a fraction Z from fractions W1 to W8 corresponding a group of fractions W as shown in a step S72. Similarly to the fraction C14, the fraction W4 is derived from the fraction E4. Therefore, it has already been found that the fraction W4 was originated from a fetal cell based on the result of the selection of the fraction D. In an actual operation, it is necessary to associate the fractions W1 to W8 with the fraction C11 to C18, respectively. The association is preferably made by using identifiers. After selecting the fraction D by the RNA analysis, it is possible to obtain data used for the later-described diagnosis from the chromosomal DNA contained in the fraction Z.

It is expected that the number of copies of RNA obtained from a single cell is larger than the number of copies of chromosomal DNA. Identification of a fetal cell based on RNA is more efficient than identification of a fetal cell based on chromosomal DNA.

Examples of a preferred method for simultaneously extracting RNA and DNA and analyzing the sequences include a G&T-seq (Genome and transcriptome sequencing) method disclosed in Non-patent Literature 3. In the G&T-seq method, chromosomal DNA and a full-length mRNA are extracted from a single cell. In this method, firstly, an isolated single cell is dissolved. Next, RNA is trapped by using a biotinylated oligo dT trapping primer for the dissolved substance. Further, DNA is separated from the dissolved substance by using magnetic beads coated with streptavidin. The trapped RNA is amplified by using a Smart-Seq2 method. Meanwhile, an MDA method is used for the amplification of the DNA.

In the method in which RNA and chromosomal DNA are simultaneously obtained, such as the G&T-seq method, the chromosomal DNA and the RNA are stored in different containers. These containers need to be attached with the above-described identifiers that associate these containers with the chromosomal DNA and the RNA.

Further, by selecting a plurality of fractions D containing RNA according to the method shown in FIG. 21, it is possible to collect the same number of fractions Z containing chromosomal DNA as the number of fractions D. Further, fractions Z are mixed with each other. In this way, it is possible to amplify chromosomal DNA in a bulk state, rather than at a single-cell level. In other words, the amplification of DNA can be started in a state where the number of copies of chromosomal DNA that are used as templates is greater than one. The amplified chromosomal DNA can be analyzed as described in the above-described embodiment. Although they can be analyzed in the bulk state as described above, the risk of mixing of DNA of maternal origin is extremely small. This is because the fact that the fraction Z is derived from fetal cells is ascertained with precision of a single-cell level. Chromosomal DNA do not necessarily have to be amplified after a plurality of fractions Z are mixed with each other. Chromosomal DNA from one fraction Z may be amplified.

[e. Acquisition of Data Used for Diagnosis]

When the fraction D contains chromosomal DNA, "e-1. Acquisition of Data Used for Diagnosis Based on Chromosomal DNA" is performed as described in <<First Embodiment>>. Data can also be obtained from the fraction Z containing chromosomal DNA in a similar manner.

When the fraction D contains RNA, the RNA sample can be used for a study of a diagnostic technique for a fetus including prenatal genetic testing.

Modified Example

A modified example can be performed as described in <<First Embodiment>>.

Example 3

Similar to the previous example, a nucleic acid to be obtained was chromosomal DNA in an Example 3. Further, the selection by labeling specific to RBCs was not performed in the cell sorting. The following processes were carried out in a manner similar to the Example 2, unless otherwise specified.

Blood collected from a pregnant woman in 24th week of pregnancy was used. The sex of the fetus was male. Similarly to the Examples 1 and 2, operations in the experiment were performed by a female experimenter. This is intended to prevent contaminations by SRY gene sequences possessed by male experimenters.

<Concentration of Maternal Blood by Blood-Cell Separation Chip>

In this example, about 8 ml of maternal blood was used. The blood was diluted to five times. Its concentration process was performed by using a chip having a micro-channel structure having functions equivalent to those of the blood-cell separation chip (the micro-channel structure) described in the Example 2.

Unlike the micro-channel structure in the chip used in the Example 2, the micro-channel structure of the chip used in the Example 3 includes only channels corresponding to the fraction Fr3 (channel diameter 15 μm), the fraction Fr4 (channel diameter 25 μm), and the fraction Fr5 (FT, flow-through). Therefore, relatively-small blood cells including non-nucleated RBCs are collected in the fraction Fr3. By removing non-nucleated RBCs by the fraction Fr3 as described above, a fraction A in which NRBCs were concentrated was obtained.

Since the processing capacity of the micro-channel structure in the chip is limited, a sample was divided into a plurality of batches and each of them is processed by an individual micro-channel structure. For batches that were still reddish after the process, which were considered to be due to non-nucleated RBCs present in the processed sample, the process using the blood-cell separation chip was performed once again. From the batches that were no longer reddish after the first process, $6.8 \times 10^6$ blood cells were obtained in total (which are referred to as a fraction A1 in this example). From the batches that were processed twice, $2.74 \times 10^6$ blood cells were obtained in total (which are referred to as a fraction A2 in this example). Cell sorting was performed by using a part of the fraction A1 and the whole fraction A2.

<Sorting of Fraction B by Cell Sorting>

Fractionation of a fraction B containing NRBCs of maternal origin and NRBCs derived from a fetus was performed as follows. The fraction A was stained with hoechst33342 and an anti-CD45 antibody. Blood cells that were positive for hoechst33342 and negative for CD45 (WBCs) were selected. Cell sorting was performed twice for blood cells in the fraction A1 by repeating the cell sorting. Cell sorting was performed only once for blood cells in the fraction A2. A fraction B containing 300 blood cells in total was obtained.

<Separation at Single-Cell Level and Extraction of Chromosomal DNA>

From the fraction B, 16 fractions C were obtained as follows. Firstly, from the fraction B, blood cells were dispensed into PCR tubes (wells) with an expected quantity of 0.5 cells/well. In this example, one dispensing volume was 0.7 μm. The dispensing was carried out by using a continuous automatic dispenser (Auto Pipettor manufactured by Eppendorf AG.). Fractions C were obtained by extracting chromosomal DNA from a blood cell in each well.

Figure 22:
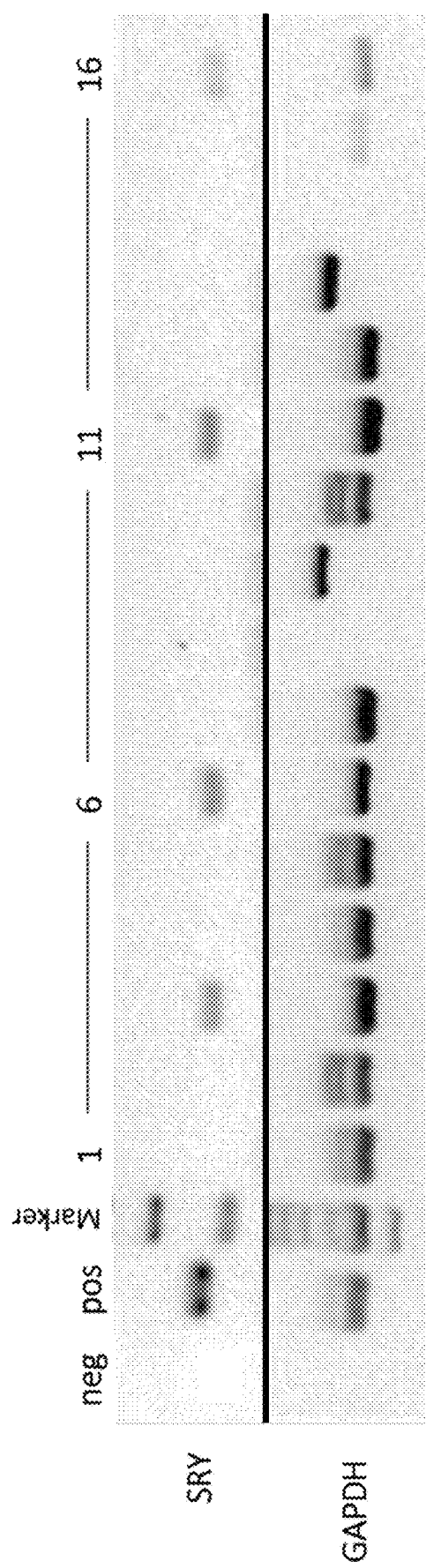
FIG. 22 is an electrophoretic image of an amplified DNA.

Whole genome amplification was performed for the chromosomal DNA in the fraction C by an MALBAC (Multiple Annealing and Looping Based Amplification Cycles) method. Using the amplified chromosomal DNA as a template, PCR amplification specific to an SRY gene sequence was performed. Further, PCR amplification specific to a GAPDH gene sequence was also performed. Since a GAPDH gene is present in an autosome, chromosomal DNA of a maternal cell is also used as a template for the GAPDH. FIG. 22 shows an electrophoretic image of a PCR product. The template and the marker are as follows.

neg: Commercially available human genome DNA of female origin (negative control)

pos: Commercially available human genomic DNA of male origin (positive control)

Marker: DNA ladder

Lanes 1-16: Amplification product by MALBAC method

As shown in FIG. 22, amplification of GAPDH was observed in lanes 1-7, 10-12, 15 and 16. The electrophoretic image indicates that chromosomal DNA derived from nucleated blood cells were distributed to these fractions C. A success rate over all the lanes, i.e., 16 lanes was 75%. In the lanes 9 and 13, bands having mobility different from those of the other lanes were observed. Although these bands are considered to be derived from amplification products by the MALBAC method, it is unknown what kind of sequence they have.

As shown in FIG. 22, amplification of SRY was observed in lanes 3, 6, 11 and 16. This indicates that chromosomal DNA derived from fetal blood cells were distributed to the fractions C. Therefore, it has been found that the fractions C shown in the lanes 3, 6 and 11 can be selected as fractions D. As described above, it has been shown that it is possible to obtain chromosomal DNA that is distinguishable at a single-cell level and is derived from a fetus by the method according to this example.

<Regarding Efficiency of Concentration in Process up to Acquisition of Fraction B>

The separation of blood cells in the fraction B at the single-cell level by a limited dilution method is performed indiscriminately irrespective of whether or not each blood cell in the fraction B has a characteristic of an NRBC. That is, blood cells are separated irrespective of whether or not each blood cell is an NRBC. Therefore, it is considered that the above-described result shown in each lane reflects a composition ratio of each blood cell in the fraction B.

Four fractions D were obtained from 16 fractions C corresponding to 16 lanes, respectively. Therefore, in an aspect, it is estimated that 25 fetal NRBCs are obtained from every 100 blood cells in the fraction B.

Four fractions D were obtained from 11 fractions C corresponding to 12 lanes in which GAPDH was amplified. Therefore, in an aspect, it is estimated that 33 fetal NRBCs are obtained from all every 100 blood cells in the fraction B.

As described above, it has been estimated that the ratio of fetal NRBCs to all the blood cells in the fraction B is at least 25% or higher and is 33% at maximum, i.e., the ratio is at a high level. It is considered that the efficiency of concentration in this example is higher than those of other methods.

Further, in the processes up to the acquisition of the fraction B shown in the above-described examples, the removal of non-nucleated RBCs using a blood-cell separation chip and the removal of WBCs by cell sorting were performed. The efficiency of concentration of fetal cells in these processes is high. An aspect according to the present invention is a method for concentrating RBCs derived from a fetus, including processes up to an acquisition of a fraction B by using a blood-cell separation chip. Such a method is a preferred concentration method for efficiently obtaining a fraction D containing a nucleic acid derived from a fetus distinguishable at a single-cell level.

This application is based upon and claims the benefit of priority from Japanese patent application No. 2016-253589, filed on Dec. 27, 2016, the disclosure of which is incorporated herein in its entirety by reference.

REFERENCE SIGNS LIST

39 GRANULE
40 CELL NUCLEI
41 NUCLEATED RED BLOOD CELLS (NRBCs)
42 NON-NUCLEATED RED BLOOD CELLS (NON-NUCLEATED RBCs)
43 WHITE BLOOD CELLS (WBCs)
44 CONTAINER
45a-45f
46 CENTRIFUGE TUBE
47 MAIN CHANNEL
48a-48c BLOOD CELL
49 SUB CHANNEL
50 BLOOD-CELL SEPARATION CHIP
51 INLET
52 MAIN CHANNEL
53 SUB CHANNEL 54a-54d OUTLET
55 OUTLET
56a-56d CHANNEL
57 SYRINGE
58 SYRINGE
59a-59d BRANCH CHANNEL
61 PLANAR CHIP
62 BLOOD CELL
74 APPARATUS
75 CHANNEL
75 TRAPPING STRUCTURES
76 REACTION STRUCTURES
77 CELL
B FRACTION
C1-C8 FRACTION
C11-C18 FRACTION
D FRACTION
E1-E8 FRACTION
F1-F3 FRACTION
Fr1-Fr5 FRACTION
FT FLOW-THROUGH
G FRACTION
M CHROMOSOME
P CHROMOSOME
S21-S26 STEP
S28-S30 STEP
S32-S33 STEP
S35-S37 STEP
S65-S66 STEP
S68-S70 STEP
S72 STEP

The invention claimed is:

1. A method for obtaining a nucleic acid derived from a fetus, comprising:
  a. specifically labeling white blood cells (WBCs) and cell nuclei in a fraction A, the fraction A being a fraction which is obtained from a maternal blood sample by fractionizing blood cells in the maternal blood sample based on either or both of their volumetric mass densities and their sizes, and in which nucleated red blood cells (NRBCs) are concentrated in a population of whole blood cells;
  b. obtaining a fraction B containing NRBCs of maternal origin and NRBCs derived from the fetus by sorting out the labeled blood cells in the fraction A by at least cell sorting, in which the sorting-out is performed so that blood cells labeled by a WBCs specific label are removed and blood cells labeled by a label specific to the cell nuclei are collected;
  c. obtaining fractions C by separating each of the blood cells in the fraction B at a single-cell level irrespective of whether or not the blood cell is a nucleated red blood cell (NRBC), and performing a process for extracting a nucleic acid for each of the blood cells separated at the single-cell level irrespective of whether or not the blood cell is an NRBC, each of the fractions C containing a nucleic acid distinguishable at the single-cell level; and
  d. selecting a fraction D containing a nucleic acid derived from the fetus distinguishable at a single-cell level from a group of the fractions C by performing a molecular biological analysis for each of the fractions C.

2. The method according to claim 1, wherein in step c, since the fraction C is obtained by a method in which it is not determined whether or not a blood cell was derived from an NRBC, it is presumed that a nucleic acid contained in the fraction D was originated from an NRBC separated at a single-cell level in an after-the-fact manner based on a determination that the nucleic acid is derived from the fetus made in the step d.

3. The method according to claim 1, wherein
the maternal blood sample is maternal blood itself or a non-concentrated sample in which NRBCs are not concentrated in a population of whole blood cells as compared to the maternal blood, and
the fraction A is a fraction obtained from the maternal blood sample by fractionating blood cells in the maternal blood sample based on their sizes and removing at least some nonnucleated RBCs from the blood cells in the maternal blood sample.

4. The method according to claim 3, wherein
blood cells of the maternal blood sample are fractionated based on their sizes by processing the maternal blood sample by using a blood-cell separation chip,
the blood-cell separation chip comprises a main channel, a sub channel connected to a side of the main channel, and a removal channel connected to a side of the main channel downstream from the sub channel, the side of the main channel on which the removal channel is connected being opposite to the side thereof on which the sub channel is connected,
the maternal blood sample flows through the main channel,
a liquid flowing out from the sub channel pushes blood cells flowing through the main channel from the side of the main channel toward the removal channel,
non-nucleated RBCs are removed from the maternal blood sample at the removal channel and NRBCs are collected from the maternal blood sample in a place in the main channel downstream from a connection point of the removal channel, so that the fraction A is obtained, and
an inscribed diameter of the removal channel is 12 to 19 µm.

5. The method according to claim 4, wherein
the blood-cell separation chip further comprises a recovery channel connected to a side of the main channel downstream from the removal channel, the side of the main channel on which the recovery channel is connected being opposite to the side thereof on which the sub channel is connected,
a liquid flowing out from the sub channel further pushes blood cells flowing through the main channel from the side of the main channel toward the recovery channel,
NRBCs are collected from the maternal blood sample at the recovery channel, so that the fraction A is obtained from the recovery channel, and
an inscribed diameter of the recovery channel is 20 to 30 µm.

6. The method according to claim 1, wherein in step c, fractions E are obtained by fractionizing the fraction B by a limited dilution method and the fraction C is obtained by performing the process for extracting the nucleic acid for each of the fractions E, each of the fractions E containing a blood cell separated at a single-cell level.

7. The method according to claim 6, further comprising:
obtaining a fraction F by sorting blood cells from the fraction B irrespective of whether or not the blood cells are NRBCs,
photographing the fraction F; and
determining whether or not the fraction F is obtained as the fraction E by checking that a blood cell separated at a single-cell level is contained in the fraction F by using an image of the fraction F, while it is not determined whether or not the blood cell separated at the single-cell level is an NRBC from the image of the fraction F.

8. The method according to claim 6, wherein
in the cell sorting, successively sorting out small amounts of fluids containing blood cells, and
dispensing the fluids into separate containers without collecting the fluids into one container again so that each container contains one blood cell.

9. The method according to claim 8, wherein
an apparatus dispenses the fluids into the separate containers, and
the apparatus is an apparatus discharges a droplet containing granular substance.

10. The method according to claim 1, wherein
in step c, the fraction C is obtained by using a fluid device comprising a channel, a plurality of trapping structures successively arranged along the channel and connected to the channel, and reaction structures provided for respective trapping structures, and
separating blood cells contained in the fraction B from each other at a single-cell level by distributing the blood cells to respective trapping structures through the channel, and after trapping the blood cells in the respective trapping structures, obtaining the fraction C in the reaction structures by dissolving the trapped cells and washing out the dissolved substance from the trapping structures toward the reaction structures.

11. The method according to claim 1, wherein
in step a, the labeling for at least the nucleic acid is performed by using fluorescent labeling, and
in step b, blood cells that have been specifically fluorescent-labeled for at least the nucleic acid in the fraction A are sorted out by cell sorting based on a fluorescence activated cell sorting method.

12. The method according to claim 1, wherein
in step c, the nucleic acid contained in the fraction C is chromosomal DNA,
in step d, the whole genome of the chromosomal DNA or a partial area in the genome is amplified in order to perform a molecular biological analysis, and
the fraction D containing DNA is sorted out as the nucleic acid derived from the fetus, the DNA being an amplification product.

13. The method according to claim 1, wherein
in step c, the nucleic acid contained in the fraction C is RNA,
the RNA is either or both of an mRNA and a non-coding RNA,
in step d, reverse transcription of the RNA is performed in order to perform a molecular biological analysis, and
the fraction D containing a cDNA is sorted out as the nucleic acid derived from the fetus, the cDNA being a reverse-transcription product.

14. The method according to claim 13, wherein
in step c, fractions W associated with respective fractions C are further obtained by extracting chromosomal DNA from each blood cell at the same time when the RNA is extracted, and
obtaining a fraction Z associated with the fraction D from a group of the fractions W as a fraction containing chromosomal DNA derived from the fetus distinguishable at a single-cell level.

15. A method comprising:
analyzing a sequence of the nucleic acid in the fraction D obtained by a method according to claim 1 by a micro-array or a sequencing method; and
obtaining data used for a diagnosis in noninvasive prenatal genetic testing from a result of the analysis.

16. The method according to claim 1, wherein
in step a, obtaining the fraction A in which WBCs are further removed from the fraction being obtained by fractionating the blood cells in the maternal blood sample based on the volumetric mass density or size, by an immunological removal method, then labeling.

17. A method for obtaining chromosomal DNA of fetal cell origin, comprising:
a. specifically labeling red blood cells (RBCs) and nucleic acids in a fraction A, the fraction A being a fraction which is obtained from a maternal blood sample and in which nucleated red blood cells (NRBCs) are concentrated in a population of whole blood cells, wherein nucleic acids are labeled at least by using fluorescent labeling when;
b. obtaining a fraction B having an increased purity of NRBCs by sorting out at least the labeled blood cells in the fraction A by cell sorting, in which blood cells in the fraction A which have been specifically fluorescent-labeled for at least nucleic acids are sorted out by cell sorting based on a fluorescence activated cell sorting method;
c. obtaining fractions C by indiscriminately separating each of blood cells in the fraction B at a single-cell level and indiscriminately and independently performing a process for extracting chromosomal DNA for each of the separated blood cells, each of the fractions C containing chromosomal DNA distinguishable at a single-cell level; and
d. selecting a fraction D containing chromosomal DNA derived from a fetus distinguishable at a single-cell level from a group of the fractions C by performing a molecular biological analysis for each of the fractions C, wherein
since the fraction C is indiscriminately obtained, it is presumed that the chromosomal DNA contained in the fraction D was originated from an NRBC separated at the single-cell level in an after-the-fact manner based on a determination that the chromosomal DNA is derived from the fetus made in the step d,
the fraction A is obtained by fractionizing blood cells in a maternal blood sample according to either their volumetric mass densities or their sizes,
in step c, fractions E are obtained by fractionizing the fraction B by a limited dilution method, each of the fractions E containing a blood cell separated at a single-cell level, and the fraction C is obtained by performing the process for extracting the chromosomal DNA for each of the fractions E, and
NRBCs of maternal origin and NRBCs derived from the fetus are contained in the fraction B.

18. The method according to claim 17, wherein
in step a, WBCs in the fraction A are specifically labeled in an additional manner, and
in step b, the fraction B is obtained by sorting out blood cells in the labeled blood cells in the fraction A by cell sorting, the fraction B being a fraction in which blood cells labeled by a WBCs specific label are removed.

19. The method according to claim 17, wherein
in step a, the labeling for RBCs is performed by magnetic labeling,
in step b, blood cells in the fraction A which have been specifically magnetic-labeled for RBCs are sorted out by cell sorting based on a cell sorting method using magnetic labeling before or after the cell sorting based on the fluorescence activated cell sorting method, or in step a, the labeling for RBCs is performed by using fluorescent labeling, and in step b, blood cells in the fraction A which have been specifically fluorescent-labeled for nucleic acids and RBCs are sorted out by cell sorting based on the fluorescence activated cell sorting method.

* * * * *